(12) United States Patent
Ilan et al.

(10) Patent No.: US 11,728,018 B2
(45) Date of Patent: Aug. 15, 2023

(54) SUBJECT-SPECIFIC SYSTEM AND METHOD FOR PREVENTION OF BODY ADAPTATION FOR CHRONIC TREATMENT OF DISEASE

(71) Applicant: OBERON SCIENCES ILAN LTD., Kefar Tavor (IL)

(72) Inventors: Yaron Ilan, Kefar Tavor (IL); Tahel Ilan Ber, Hod Hasharon (IL)

(73) Assignee: OBERON SCIENCES ILAN LTD, Kefar Tavor (IL)

( * ) Notice: Subject to any disclaimer, the term of this patent is extended or adjusted under 35 U.S.C. 154(b) by 0 days.

(21) Appl. No.: 16/627,609

(22) PCT Filed: Jul. 1, 2018

(86) PCT No.: PCT/IL2018/050711
§ 371 (c)(1),
(2) Date: Dec. 30, 2019

(87) PCT Pub. No.: WO2019/008571
PCT Pub. Date: Jan. 10, 2019

(65) Prior Publication Data
US 2020/0143924 A1    May 7, 2020

Related U.S. Application Data

(60) Provisional application No. 62/528,108, filed on Jul. 2, 2017.

(51) Int. Cl.
*G16H 20/10* (2018.01)
*G16H 50/20* (2018.01)
*G16H 70/20* (2018.01)

(52) U.S. Cl.
CPC ............. *G16H 20/10* (2018.01); *G16H 50/20* (2018.01); *G16H 70/20* (2018.01)

(58) Field of Classification Search
None
See application file for complete search history.

(56) References Cited

U.S. PATENT DOCUMENTS

2007/0276441 A1* 11/2007 Goetz ............... A61N 1/37252
607/2
2007/0287931 A1   12/2007 DiLorenzo
(Continued)

FOREIGN PATENT DOCUMENTS

WO   2009018132       2/2009
WO   2012129574 A2    9/2012
(Continued)

OTHER PUBLICATIONS

Xu et al., Association of Microtubule Dynamics with Chronic Epilepsy, Jun. 4, 2015, Mol Neurobiol (2016) 53:5013-5024, DOI 10.1007/s12035-015-9431—(Year: 2016).*
(Continued)

*Primary Examiner* — Devin C Hein
(74) *Attorney, Agent, or Firm* — The Roy Gross Law Firm, LLC; Roy Gross

(57) ABSTRACT

There are provided herein a system and a computer implemented method for preventing, mitigating or treating partial/complete loss of effect of one or more drugs or medical devices administered to or used by a subject in need thereof due to adaptation, tolerance, and/or tachyphylaxis, and/or for preventing, mitigating or treating non-responsiveness to one or more drugs, maximizing therapeutic effect of one or more drugs, or for improving target or non-target organ/organs response to therapy, the system/method include (processing circuit configured to): receiving a plurality of physiological or pathological parameters of the subject; applying a machine learning algorithm on the plurality of physiological or pathological parameters; and determining a subject-specific administration regimen of a drug or a medical
(Continued)

treatment, wherein the administration regimen comprises drug administration parameters, cell/tissue/organ stimulation parameters, adjuvant parameters or any combination thereof; wherein the administration regimen is irregular.

17 Claims, 10 Drawing Sheets

(56) References Cited

U.S. PATENT DOCUMENTS

| | | | |
|---|---|---|---|
| 2008/0097553 | A1 | 4/2008 | John |
| 2011/0208271 | A1* | 8/2011 | Dobak ............... A61N 1/36007 607/72 |
| 2011/0218407 | A1 | 9/2011 | Haberman et al. |
| 2013/0034837 | A1 | 2/2013 | Clapp et al. |
| 2013/0035740 | A1 | 2/2013 | Sharma et al. |
| 2014/0058317 | A1* | 2/2014 | Imran ............... A61B 1/00082 604/65 |
| 2014/0099614 | A1 | 4/2014 | Hu et al. |
| 2014/0127650 | A1 | 5/2014 | Utter, II |
| 2015/0321000 | A1 | 11/2015 | Rosenbluth et al. |
| 2016/0262693 | A1 | 9/2016 | Sheon |
| 2017/0220751 | A1 | 8/2017 | Davis et al. |
| 2017/0296116 | A1 | 10/2017 | McCarthy et al. |

FOREIGN PATENT DOCUMENTS

| | | |
|---|---|---|
| WO | 2019008571 A1 | 1/2019 |
| WO | WO-2021041469 A1 * | 3/2021 |
| WO | WO-2021087456 A1 * | 5/2021 |

OTHER PUBLICATIONS

Tifft et al., Stemming the tide: glycosphingolipid synthesis inhibitors as therapy for storage diseases, Aug. 29, 2000, Glycobiology, vol. 10, pp. 1249-1258 (Year: 2000).*
Sareen et al., A Cloud-Based Seizure Alert System for Epileptic Patients That Uses Higher-Order Statistics, computing in Science & Engineering, vol. 18, No. 5, pp. 56-67, Sep.-Oct. 2016, doi: 10.1109/MCSE.2016.82. (Year: 2016).*
Deng, Chunqin and Julia Graz. "Paper 267-27 Generating Randomization Schedules Using SAS Programming." (2002). (Year: 2002).*
Ward, et al., "State and Regional Prevalence of Diagnosed Multiple Chronic Conditions Among Adults Aged > 18 Years—United States 2014", MMRW—Morbidity and Mortality Weekly Report vol. 65 No. 29: 735-738, (2016).
Bespalov, et al., "Drug Tolerance: A Known Unknown in Translational Neuroscience", Trends in Pharmacological Sciences, vol. 37 No. 5: 364-378 (2016).
Löscher, et al., "Experimental and Clinical Evidence for Loss of Effect (Tolerance) during Prolonged Treatment with Antiepileptic Drugs", Epilepsia vol. 47 No. 8: 1253-84 (2006).
Widdess-Walsh, Peter "Antiepileptic Drug Resistance and Tolerance in Epilepsy", Reviews in Neurological Diseases, vol. 4 No. 4: 194-202 (2007).
Catan, et al., "Prescription for Addiction", Wall Street Journal Online, published Oct. 5, 2012, accessed Nov. 5, 2012.
Facchini, et al., "Beta-Blockers and Nitrates: Pharmacotherapy and Indications," Cardiovascular & Hematological Agents in Medicinal Chemistry vol. 13 No. 1: 25-30 (2015).
Antoniou, et al., "Management of Hypertensive Patients with Multiple Drug Intolerances: A Single-Center Experience of a Novel Treatment Algorithm", The Journal of Clinical Hypertension vol. 18, No. 2 (2015).
Boucher, et al., "Insulin Receptor Signaling in Normal and Insulin-Resistant States", Cold Spring Harbor Perspectives in Biology vol. 6, (2014).
Roussel, et al., "Molecular mechanisms redirecting the GLP-1 receptor signaling profile in pancreatic β-cells during type 2 diabetes", Hormone Molecular Biology Clinical Investigation vol. 26 No. 2: 87-95 (2016).
Nakamura, et al., "Present Status of Clinical Deployment of Glucokinase Activators", Journal of Diabetes Investigation, vol. 6 No. 2: 124-32 (2015).
Roda, et al., "Loss of Response to Anti-TNFs: Definition, Epidemiology, and Management", Clinical and Translational Gastroenterology vol. 7 (2016).
Qiu, et al., "Systematic review with meta-analysis: loss of response and requirement of anti-TNFα dose intensificaiton in Crohn's disease", Journal of Gastroenterology vol. 52 (2017).
Lautebach, Edward "Treatment Resistant Depression with Loss of Antidepressant Response: Rapid-Acting Antidepressant Action of Dextromethorphan, A Possible Treatment Bridging Molecule", Psychopharmacology Bulletin, vol. 46 No. 2: 53-5 (2016).
Targum, Stephen D. "Identification and Treatment of Antidepressant Tachyphylaxis", Innovations in Clinical Neuroscience, vol. 11 No. 3-4: 24-28 (2014).
Richman, et al., "The Prevalence of Antiretroviral Drug Resistance in the United States", AIDS, vol. 18: 1393-1401 (2004).
Ventola, C. Lee "The Antibiotic Resistance Crisis: Part 1: Causes and Threats", P & T: A Peer-Reviewed Journal for Formulary Management, vol. 40 No. 4: 277-283 (2015).
Gottesman, Michael M. "Mechanisms of Cancer Drug Resistance", Annual Review of Medicine vol. 53: 615-627 (2002).
Majumder, et al. "Predicting Clinical Response to Anticancer Drugs Using an Ex Vivo Platform that captures Tumor Heterogeneity", Nature Communications, vol. 6 (2015).
Smid, et al., "Biochemical Response to Substrate Reduction Therapy versus Enzyme Replacement Therapy in Gaucher Disease Type 1 Patients", Orphanet Journal of Rare Diseases, vol. 11 No. 28 (2016).
Gajofatto, et al. "Treatment Strategies for Multiple Sclerosis: When to start, When to change, When to stop?", World Journal of Clinical Cases, vol. 3 Issue 7: 545-555 (2015).
Zee, et al. "Circadian Rhythm Abnormalities", Continuum vol. 19: 132-147 (2013).
Leung, et al. "Colchicine—Update on Mechanisms of Action and Therapeutic Uses", Seminars in Arthritis and Rheumatism vol. 45 No. 3: 341-50 (2015).
Stack, et al. "Colchicine: New Insights to an Old Drug", American Journal of Therapeutics vol. 22: e151-e157 (2015).
Wechalekar, et al., "The Efficacy and Safety of Treatments for Acute Gout: Results from a Series of Systematic Literature Reviews including Cochrane Reviews on Intraarticular Glucocorticoids, Colchicine, Nonsteroidal Antiinflammatory Drugs and Interleukin-1 inhibitors", The Journal of Rheumatology, vol. 92: 15-25 (2014).
Hemkins, et al. "Colchicine for prevention of cardiovascular events", Cochrane Database of Systematic Reviews, Issue 1, (2016).
Rigante, et al., "The Pharmacologic Basis of Treatment with Colchicine in Children with Familial Mediterranean Fever", European Review for Medical and Pharmacological Sciences, vol. 10: 173-8 (2006).
Lu, et al. "An Overview of Tubulin Inhibitors That Interact with the Colchicine Binding Site", Pharmaceutical Research, vol. 29 No. 11: 2943-71 (2012).
Finkelstein, et al., "Colchicine poisoning: the dark side of an ancient drug", Clinical Toxicology vol. 48: 407-14 (2010).
Terkeltaub, Robert "Colchicine update: 2008", Seminars in Arthritis Rheumatism, vol. 38 411-19 (2009).
Schlesinger, Naomi "Reassessing the safety of intravenous and compounded injectable colchicine in acute gout treatment", Expert Opinion on Drug Safety 6:6, 625-629 (2007).
Wilbur, et al., "Colchicine Myotoxicity: Case Reports and Literature Review", Pharmacotherapy, vol. 24: 1784-92 (2004).
Gasparyan, et al. "Colchicine as an anti-inflammatory and cardioprotective agent", Expert Opinion on Drug Metabolism & Toxicology. 11: 1781-94 (2015).
Nuki, George "Colchicine: Its Mechanism of Action and Efficacy in Crystal-Induced Inflammation", Current Rheumatology Reports, vol. 10: 218-227 (2008).
Bhattacharyya, et al., "Anti-Mitotic Activity of Colchicine and the Structural Basis for Its Interaction with Tubulin", Medicinal Research Reviews, vol. 28 No. 1: 155-183 (2008).
Niel, et al. "Colchicine today", Joint Bone Spine, vol. 73: 672-8 (2006).

(56) References Cited

OTHER PUBLICATIONS

Mundy et al. (1990) Neurotoxic effects of colchicine, Neurotoxicology, 11: 539-47.

Nidorf, et al. "Colchicine for Secondary Prevention of Cardiovascular Disease", Current Atherosclerosis Reports vol. 16: 391 (2014).

Lange, et al. "Current Aspects of Colchicine Therapy Classical Indications and New Therapeutic Uses", European Journal of Medical Research vol. 6: 150-160 (2001).

Das, Un "Colchicine in Diabetes Mellitus", The Journal of the Association of Physicians of India, vol. 41 No. 4: 213 (1993).

Rudd, et al., "Increases in Drug and Opioid Overdose Deaths—United States, 2000-2004", Centers for Disease Control and Prevention Morbidity and Mortality Weekly Report, pp. 1323-1327 (2016).

International Search Report, International Application No. PCT/IL2018/050711, dated Oct. 9, 2018.

"Non-Communicable Diseases Fact sheet", World Health Organization, Jan. 2015. Retrieved Apr. 5, 2016.

Moore et al (2012)Leisure Time Physical Activity of Moderate to Vigorous Intensity and Mortality: A Large Pooled Cohort Analysis, Public Library of Science, e1001335.

Byrne et al (2005) Metabolic equivalent: one size does not fit all, Journal of Applied Physiology, vol. 99, No. 3: 1112-1114.

Strong, William B (2005) Evidence Based Physical Activity for School-Age Youth, J of Pediatrics, vol. 146, Issue 6: 732-737.

Malina, C M (1991) Fitness and performance: adult health and the culture of youth, new paradigms? In Park & Eckert, New Possibilities, new Paradigms?, Amn Academy of Physical Education Pepers, No. 24, Champaign IL, Human Kinetics Publishers, pp. 30-38.

Training routines for Olympic track sprinters: http://www.livestrong.com/article/467983-training-routines-for-olympic-track-sprinters.

Heinonen M S (1996) Randomised controlled trial of effect of high-impact exercise on selected risk factors for osteoporotic fractures, Lancet, vol. 348, Issue 9058, pp. 1343-1347.

Clement, D B (1993) Exercise-induced Stress Injuries to the Femur, Int J Sports Med 14(6): 347-352.

Asrar Ul Haq M et al (2015) Clinical Utility of Exercise Training in Heart Failure with Reduced and Preserved Ejection Fraction, Clin Med Insights Cardiol 9:1-9.

De Maeyer et al (2013) Exercise Training in Chronic Heart Failure, The Adv Chronic Dis, 4(3: 105-117.

Pizzie, Rachel (2014) Physical Activity and Cognitive Trajectories in Cognitivel Normal Adults: The Adult Children Study, Alzheimer Dis Assoc Disorder, 28(1): 50-57.

Hill et al (2013) Ghrelin and peptide YY increase with weight loss during a 12-month intervention to reduce dietary energy density in obese women, Peptides, 49: 128-144.

http://www.who.int/dietphysicalactivity/factsheet_adults/en/.

Asthma Overview: https://www.ncbi.nlm.nih.gov/pubmedhealth/PMH00720701/.

DelGiacco et al (2015) Exercise and Asthma: an overview, European Clinical Respiratory Journal; https://www.ncbi.nlm.nih.gov/pmc/articles/PMC4653278/.

* cited by examiner

SUBJECT-SPECIFIC SYSTEM AND METHOD FOR PREVENTION OF BODY ADAPTATION FOR CHRONIC TREATMENT OF DISEASE

RELATED APPLICATIONS

This application is a National Phase of PCT Patent Application No. PCT/IL2018/050711 having International filing date of Jul. 1, 2018 which claims the benefit of priority of U.S. Provisional Application No. 62/528,108 filed on Jul. 2, 2017 entitled A SUBJECT-SPECIFIC SYSTEM AND METHOD FOR PREVENTION OF BODY ADAPTATION FOR CHRONIC TREATMENT OF DISEASE. The contents of the above applications are all incorporated by reference as if fully set forth herein in their entirety.

TECHNICAL FIELD

The present disclosure generally relates to the field of prevention of body adaptation to any type of chronic treatment of disease.

BACKGROUND

Treatment of chronic diseases commonly follows a set regimen intended to affect physiological or pathological change. It is carried out based on pre-determined protocols, within therapeutic windows, or efficacy window, such that once a certain treatment protocol is prescribed/configured, it stays identical until the treatment is finished or non-responsiveness occurs. This is mainly in the case of chronic diseases such as epilepsy, diabetes, pain, or hypertension. While this method of treatment shows efficacy in some cases, it is often less effective or not effective at all in others. This is due to adaptation processes that occurs in the body and/or in the target organ to prolonged exposure to drugs, or development of any type of tolerance, and/or tachyphylaxis, prohibiting maximal effect and long-lasting effect.

A chronic condition is a human health condition or disease that is persistent or otherwise long lasting in its effects or a disease that comes with time. The term chronic is often applied when the course of the disease lasts for more than three months. Common chronic diseases including epilepsy, arthritis, asthma, cancer, COPD, diabetes, fatty liver, and viral diseases such as HIV/AIDS. In the United States 25% of adults, have at least two chronic conditions. (Ward, B W; Black, L I (29 Jul. 2016). *"State and Regional Prevalence of Diagnosed Multiple Chronic Conditions Among Adults Aged ≥18 Years—United States, 2014."* MMWR. Morbidity and mortality weekly report. 65 (29): 735-8. doi: 10.15585/mmwr.mm6529a3). Chronic diseases constitute a major cause of mortality, with the World Health Organization (WHO) attributing 38 million deaths a year to non-communicable diseases. (*Non-communicable diseases. Fact sheet"*. World Health Organization. January 2015. Retrieved Apr. 5, 2016).

Most subjects with chronic disease require long term treatment with various medications. For many of these medications or modes of therapy, loss of the maximal effect or even all the effect may occur following a certain period, which is associated with several mechanisms. There are many possible causes for losing an effect of a drug or a treatment provided by a medical device. Some of which are not well understood. Some may involve pharmacological tolerance, and some involve adaptation of the targeted organ, or pathway, to the treatment. Part of the loss of the effect may be due to drug tolerance which is a pharmacological concept describing subjects' reduced reaction to a drug following its repeated use. Increasing its dosage may re-amplify the drug's effects; however, this may further accelerate tolerance, further reducing the drug's effects or may be associated with side effects without major impact on the effect of therapy thus inducing a vicious cycle (Bespalov, Anton; Midler, Reinhold; Relo, Ana-Lucia; Hudzik, Thomas (2016 Jul. 1). *"Drug Tolerance: A Known Unknown in Translational Neuroscience"*. Trends in Pharmacological Sciences. 37 (5): 364-378). Development of tolerance (i.e., the reduction in response to a drug after repeated administration) is an adaptive response of the body to prolonged exposure to the drug, and tolerance (*Epilepsia.* 2006 August; 47(8):1253-84. *Experimental and clinical evidence for loss of effect (tolerance) during prolonged treatment with anti-epileptic drugs.* Löscher W1, Schmidt D).

The adaptation and habituation to a treatment can be at the molecular, cellular, or whole organ level. It depends on factors associated with the disease, the drug, and/or the subjects. It may be a result of a tumor promoting bypassing pathways that prohibit an effect of an anti-tumor therapy which affects a pathway. Such that while some subjects will lose the effect of a drug others many not. A disease process may find a way to continue by bypassing the effect of a chronic drug. For many chronic therapies, adaptation of the target organ prohibits maximal effect of the drug or is associated with total loss of an effect of a drug or that of a medical device. Adaptation develops to some drugs much more rapidly than to others. The extent of adaptation or tolerance depends on the disease, the drug, and individual genetic and other factors, as well as on the type of drug, dosage, and duration of treatment. Adaptation may occur within a relatively short period of time, part of non-effectiveness, or minimal efficacy to any drug can be attributed to this process.

Pharmacokinetic (metabolic) tolerance may occur due to induction of drug-metabolizing enzymes. Pharmacodynamics (functional) tolerance is due to "adaptation" of the drugs-targets (e.g., by loss of receptor sensitivity). Functional tolerance may lead to complete loss of drug activity and cross-tolerance to other drugs with similar or different mechanisms. Tachyphylaxis is a sudden onset drug tolerance which is not dose dependent. In addition, circadian rhythm due to endocrinological or to any other mechanism is relevant for adaptation to therapy for some treatments.

Examples for lost effect of the drug following prolonged administration:

a. Tolerance for anti-epileptic drugs: Data shows that almost all first-, second-, and third-generation anti-epileptic drugs lose their antiepileptic activity during prolonged treatment at some extent. Development of tolerance to the antiepileptic activity is an important reason for failure of drug treatment (*Rev Neurol Dis.* 2007 Fall; 4(4): 194-202. *Antiepileptic drug resistance and tolerance in epilepsy*).

b. Loss of effect of painkillers: Chronic use of painkillers and adaptation of various types of these medications is a major unmet need leading to the problem of a need for increasing dosages. The prevalence of narcotic painkillers, opioids, has increased exponentially, and so has the number of deaths related to use of these medications. The consequence of this orientation to increasing prescriptions of opioids for treatment of chronic pain has had the unintended consequence of leading to a rapid increase death from opioid overdose (poisoning). Most people who take narcotic pain killers will develop some tolerance to the medications if they use them for more than 2 to 4 weeks, and if taken on a daily basis for any longer than this time period, most people will also develop some habituation, urge to continue taking the medication on a daily basis. In subjects who have developed a tolerance and habituation, they will have withdrawal symptoms when they discontinue taking the narcotics. This withdrawal process is a natural consequence of taking the medication and does not mean that the individual is addicted to narcotics. Abuse of narcotic medications defined as taking more than the prescribed amount. Although all addicts are abusers, not all abuse is done by addicts. Narcotic medications causes a down regulation of the Mu receptors in the brain, and with less receptors it takes more narcotic-like molecules, either endogenous or in pill form, for subjects to get the same feeling. Taking narcotic medications may paradoxically cause subjects to feel more pain as the loss of receptors does not allow the body to regulate the feeling of pain as well. A process known as hyperalgesia. This down regulation leads to tolerance and a need for increased narcotics over time to get the same levels of pain relief (*Increases in Drug and Opioid Overdose Deaths—United States,* 2000-2014," published Jan. 1, 2016, accessed Jun. 3, 2016; *CDC Grand Rounds: prescription Drug Overdoses—a U.S. Epidemic,"* Centers for Disease Control and Prevention, published Jan. 13, 2012, accessed Nov. 5, 2012; Catan T, Barrett D, and Martin T, "*Prescription for Addiction,"* Wall Street Journal Online*, published Oct. 5, 2012, accessed Nov. 5, 2012.

c. Losing the effect of drugs that work on the heart and blood vessels: Nitrates: While their efficacy in relieving angina pectoris symptoms in acute settings and in preventing angina before physical or emotional stress is undisputed, the chronic use of nitrates has been associated with tolerance (*Cardiovasc Hematol Agents Med Chem.* 2015; 13(1): 25-30. *Beta-Blockers and Nitrates: Pharmacotherapy and Indications.* Facchini E, Degiovanni A, Cavallino C, Lupi A, Rognoni A I, Bongo A S.)

d. Losing the effect of anti-hypertensive medications: Treatment of hypertension: Despite the availability of numerous medication classes that lower blood pressure (BP), hypertension is adequately controlled to guideline-recommended levels in <50% of treated subjects. One of the causes for that is multiple drug tolerances (2015 *Journal of clinical Hypertension Management of Hypertensive Patients with Multiple Drug Intolerances: A Single-Center Experience of a Novel Treatment Algorithm Sotiris Antoniou*).

e. Losing the effect of anti-diabetic drugs: Insulin resistance which is due to an effect on the insulin receptor and require the increase in the dose of insulin in many type 2 diabetics over time (*Cold Spring Harb. Perspect. Biol.* 2014; 6: a009191 *Insulin receptor signaling in normal and insulin-resistant states* Boucher, J. et al); Treatment of diabetes using any type of drugs including: sodium-glucose transporters (SGLTs) including: Canagliflozin (Invokana); Dapagliflozin (Farxiga); Empagliflozin (Jardiance); Long Acting Insulin; GLP 1 suchs as exenatide (Byetta) and liraglutide (Victoza), at least once a day; Lixisenatide (Adlyxin) once a day injection; Drugs that last for 7 days: Albiglutide (Tanzeum); Dulaglutide (Trulicity); Extended-release exenatide (Bydureon); DPP-4 inhibitors include medications with: Alogliptin (Nesina); Alogliptin and metformin (Kazano); Alogliptin and pioglitazone (Oseni); Linagliptin (Jentadueto); Linagliptin and metformin (Tradjenta); Saxagliptin (Ongylza); Saxagliptin and metformin (Kombiglyze); Sitagliptin (Januvia); Sitagliptin and metformin (Janumet). For several of these, such as GLP-1 analogues, glucokinase activators, and DPP4 inhibitors, a loss of their effectiveness over time is shown in some subjects (Roussel M, Mathieu J, Dalle S. *Horm Mol Biol Clin Investig.* 2016 May 1; 26(2): 87-95. doi: 10.1515/hmbci-2015-071. *Molecular mechanisms redirecting the GLP-*1 *receptor signaling profile in pancreatic β-cells during type* 2 *diabetes;* Nakamura A, Terauchi Y. *Present status of clinical deployment of glucokinase activators. J Diabetes Investig.* 2015 March; 6(2):124-32. 2014).

f. Losing the effect of immune modulatory and anti-inflammatory drugs: Rheumatoid arthritis; multiple sclerosis; inflammatory bowel diseases; psoriasis; such as non-responsiveness to anti TNF: Overall, around one-third of Crohn's disease subjects experience a loss of response and required dose intensification in primary anti-TNF-α responders (Roda G., Jharap B., Neeraj N, Colombel J-F. *Loss of response to anti-TNFs: definition, epidemiology, and management.* Clinical and Translational Gastroenterology. 2016; 7(1, article e135) doi: 10.1038/ctg.2015.63; Qiu Y, *Systematic review with meta-analysis: loss of response and requirement of anti-TNFα dose intensification in Crohn's disease. J Gastroenterol.* 2017 doi: 10.1007/s00535-017-1324-3).

g. Losing the effect of anti-depressant medications. Anti-depressant tachyphylaxis is a condition in which a depressed subject loses a previously effective antidepressant treatment response despite staying on the same drug and dosage for maintenance treatment. Antidepressant tachyphylaxis is a form of relapse related to evolving drug tolerance, but there are other reasons for the loss of treatment response unrelated to tolerance ((*Psychopharmacology Bull.* 2016 Aug. 15; 46(2): 53-58. PMCID: PMC5044468 *Treatment Resistant Depression with Loss of Antidepressant Response: Rapid-Acting Antidepressant Action of Dextromethorphan, A Possible Treatment Bridging Molecule.* E C. Lauterbach et al.; Steven D. Targum *Identification and Treatment of Antidepressant Tachyphylaxis. Innov Clin Neurosci.* 2014 Mar.-Apr. 11(3-4): 24-28).

h. Losing the effect of anti-viral medications and inducing of drug-resistant mutations, such as treatment of HIV, HBV or HCV infections. The estimated the percentage of the American HIV positive population with some form of drug resistance to be 76.3% (Richman, D. D., S. C. Morton, T Wrin, N. Hellmann, S. Berry, M. F. Shapiro, and S. A. Bozzette. 2004. *The prevalence of antiretroviral drug resistance in the United States. AIDS.* 18: 1393-1401).

i. Losing the effect of antibiotics and the induction of antibiotic: Increasing bacterial resistance is linked with the volume of antibiotic prescribed, and other reasons ((Ventola C L. *The antibiotic resistance crisis: part* 1*: causes and threats. P T.* 2015; 40(4): 277-283; Pechére J C (September 2001). *Patients' interviews and misuse of antibiotics. Clin. Infect. Dis.* 33 *Suppl* 3*: S*170-3).

j. Losing the effect of anti-cancer medications: Predicting clinical response to anticancer drugs remains a major challenge in cancer treatment. Intratumoral heterogeneity contribute to the variability of response to chemotherapy, which is not captured by the existing cancer cell biomarker-based approaches. Genetic and epigenetic factors, tumor microenvironment, are possible causes. For example, epidermal growth factor receptor (EGFR) inhibitors, cetuximab and panitumumab, for metastatic colorectal carcinoma with wild-type KRAS, but provide clinical benefit in only 10-20% of selected subjects (*Annu Rev Med.* 2002; 53:615-27. *Mechanisms of cancer drug resistance.* Gottesman M M et al.; Biswanath Majumder Predicting clinical response to anticancer drugs using an ex vivo platform that captures tumor heterogeneity Nature Communications 6: 6169, (2015).

k. Treatment of inborn error of metabolism: enzyme deficiency such as Gaucher disease, Fabry disease: Enzyme replacement therapy does not completely prevent bone complications and subjects experience despite treatment additional bone complications (Bouwien E. Smid, *Biochemical response to substrate reduction therapy versus enzyme replacement therapy in Gaucher disease type* 1 *patients. Orphanet Journal of Rare Diseases* 201611:28 l. Non-responsiveness or loss of effect of treatment of neurological disorders: Huntington diseases; ALS; Multiple sclerosis, Alzheimer's disease: Currently approved disease-modifying therapies for multiple sclerosis are immunomodulatory and have much variably in efficacy. In addition, they have limited efficacy in preventing the transition to the progressive phase of the disease. Individual response to existing therapies varies significantly across subjects and 30-80% discontinue therapy (Alberto Gajofatto *Treatment strategies for multiple sclerosis: When to start, when to change, when to stop? World J Clin Cases.* 2015 Jul. 16; 3(7): 545-555).

m. Non-responsiveness or loss of effect of treatments that target the microbiome, for alleviation of microbiome-related diseases.

n. Non-responsiveness or loss of effect of treatments of circadian rhythm related diseases including jet lag, desynchronosis or circadian dysrhythmia (Zee P C, Attarian H, Videnovic A. *Circadian rhythm abnormalities. Continuum* (Minneap Minn.) 2013; 19 (1 *Sleep Disorders*): 132-147).

o. Non-responsiveness to chronic lung medications such as agonist for the beta-2 adrenergic receptor, Salbutamol, treatment for asthma. With regular use, some subjects experience a significant decline in bronchodilator response.

There is thus a need in the art for more effective drug regimens that take into consideration the variability between subjects and their physiological reaction to various drugs and subjects' circadian rhythm, and the loss of an effect or maximal response to a treatment using drugs or medical devices in chronic diseases.

Disclosed herein is inter alia a method for overcoming organ adaptation for any type of drug or medical device-based therapy by using a subject-specific, disease-tailored, and/or drug-tailored algorithm. As organ adaptation is expected to be different among different individuals, the claim is made that every subject should have a specific tailor-made algorithm. Similarly, every disease and every drug should have their specific algorithm.

Several types of therapies and methods for overcoming adaptation are claimed by developing subject-specific and/or drug and/or disease-specific algorithm based on one of the followings:

1. An algorithm for drugs the administration of which does not depend on a precise time of administration, such as drugs which are administered once a day. For these drugs, an irregular algorithm-based therapy is designed for improvement of the response rate. These include for example anti diabetic, anti-inflammatory and anti-neoplastic drugs.

2. An algorithm for drugs the pharmacokinetics of which are of high importance and the therapeutic window narrow: For these drugs, irregular dose, time, and/or mode of administration will be set within the therapeutic window.

3. An algorithm for drugs involving a physiological or pathological circadian rhythm including jet lag, referred to as desynchronosis or circadian dysrhythmia. For these drugs a new treatment regimen to overcome a physiological or pathological circadian rhythm is designed.

4. An algorithm for using adjuvant medications with the drug or treatment, which can prevent, alleviate, or overcome the adaptation to therapy. These adjuvants can be any type of drug that targets the microtubules and/or the glycosphingolipid pathway and/or any type of physiological or pathological metabolite, irrespective whether the cell cytoskeleton has a role in the pathogenesis of the chronic condition.

5. An algorithm for drugs that target the microtubules using a low dose that has no systemic effect on the microtubules nor on the immune system for any chronic disease including microbiome-associated diseases.

6. An algorithm for generation any type of stimulation delivered to any organ.

SUMMARY

The following embodiments and aspects thereof are described and illustrated in conjunction with systems, tools and methods, which meant to be exemplary and illustrative, not limiting in scope. In various embodiments, one or more of the above-described problems have been reduced or eliminated, while other embodiments are directed to other advantages or improvements.

The embodiments show that personalized-based treatment regimen of irregular drug or therapy administration and/or stimulation regimen and/or use of adjuvant drugs, improves response rate and/or prevents or ameliorates target organ adaptation, improving the effect of chronic treatment. The disclosed algorithm is disease-specific, drug-specific, and subject-specific.

The deep machine-learning algorithm can benefit from learning from large number of subjects with the same disease and the same treatment, as well enable to tailor therapies which are more beneficial for certain subjects. The cell phone-based application, or any other mode of application, will send an alert to the subject on when to take the required medication, how, and which dose to use and which combination of drugs and/or to use adjuvant drugs, to be used. A similar application will apply to any type of medical device used for diagnosis or treatment.

According to some embodiments, there are provided herein devices, systems and methods for generation of treatment algorithms for prevention of adaptation to therapy, or loss of effect of therapy, or non-responsiveness to therapy, via altering the dose, and/or time of administration and/or combining different drugs or any other type of a change which is related to a treatment for improving the long term effect of the drug or medical device-based, or any type of treatment and prevention of adaptation or prevention of loss of a maximal effect of all types of chronic therapies by drugs and medical devices.

According to some embodiments, there is provided any organ stimulation, wherein the stimulation parameters are updated within the treatment/stimulation period, for personalizing the stimulation parameters and increasing the accuracy and/or efficacy of the stimulation treatment for achieving the desired physiological goal as well as to prevent long-term adaptation or for ensuing prolong maximal effect of drug therapy on the target organ or physiological pathway, is within the scope of this disclosure.

According to some embodiments, there is provided an algorithm for adding adjuvant drugs that target the microtubules in any dosage, including low dosages which have no effect on the systemic microtubules nor on the immune system, and which are below the therapeutic window, can prevent, or treat adaptation to therapy, and improve efficacy of all types of chronic therapies, whether or not the chronic disease is associated with any derangement of the microtubules.

According to some embodiments, there is provided a computer implemented method for preventing, mitigating or treating partial/complete loss of effect of one or more drugs or medical devices administered to or used by a subject in need thereof due to adaptation, tolerance, and/or tachyphylaxis, and/or for preventing, mitigating or treating non-responsiveness to one or more drugs, maximizing therapeutic effect of one or more drugs, or for improving target or non-target organ/organs response to therapy. According to some embodiments, the method includes receiving a plurality of physiological or pathological parameters of the subject, applying a machine learning algorithm on the plurality of physiological or pathological parameters, and determining a subject-specific administration regimen of a drug or a medical treatment, wherein the administration regimen includes drug administration parameters, cell/tissue/organ stimulation parameters, adjuvant parameters or any combination thereof, and wherein the administration regimen is irregular. According to some embodiments, the method may further include updating the administration regimen based on newly received values of the plurality of physiological or pathological parameters. According to some embodiments, the medical treatment is organ stimulation and wherein the administration regimen includes cell/tissue/organ stimulation parameters. According to some embodiments, the method may further include updating the stimulation parameters based on data being continuously learned from the subject and/or by other users. According to some embodiments, the machine learning algorithm may further consider personal data selected from, but not limited to: age, weight, periodic caloric intake and output, gender, ethnicity, geography, pathological history/state, temperature, metabolic rate, glucose levels, blood tests and any physiological or any pathological or physiological biomarkers or parameters that can be measured, that are directly or indirectly associated with the physiological target or with the chronic disease. According to some embodiments, at least one of the physiological or pathological parameters is obtained from a sensor. According to some embodiments, the method may further include notifying the subject regarding the administration regimen, wherein the notifying includes informing about time, dose and/or method of administration of one or more drugs and/or one or more adjuvant drugs. According to some embodiments, the notifying is in real time. According to some embodiments, the method may further include stimulating a tissue or an organ of the subject utilizing a wearable/swallowed/implanted device. According to some embodiments, the method may further include administering one or more drugs to the subject. According to some embodiments, the method may be used for the treatment of obesity, infectious, metabolic, endocrinology, malignant, immune-mediated, inflammatory condition, inborn error of metabolism, pain, microbiome-related disorders, neurological disease, fibrosis in any organ, any type of disease in which circadian rhythm is relevant or any combination thereof. According to some embodiments, the drug is a drug that targets microtubules. According to some embodiments, the drug is a drug that targets glycosphingolipids.

According to some embodiments, there is provided a system for preventing, mitigating or treating partial/complete loss of effect of one or more drug or medical devices administered to or used by a subject in need thereof due to adaptation, tolerance, and/or tachyphylaxis, and/or for preventing, mitigating or treating non-responsiveness to one or more drugs, maximizing therapeutic effect of one or more drugs, improving target or non-target organ/organs response to therapy. According to some embodiments, the system includes a processing circuit configured to receive a plurality of physiological or pathological parameters of the subject, apply a machine learning algorithm on the plurality of physiological or pathological parameters, and determine a subject-specific administration regimen of the one or more drugs or medical treatments, wherein the administration regimen includes drug administration parameters, cell/tissue/organ stimulation parameters, adjuvant parameters or any combination thereof, and wherein the administration regimen is irregular. According to some embodiments, the system may further include a stimulation inducer. According to some embodiments, the stimulation inducer includes a pill, configured to be swallowed, transplanted or otherwise reach a target body region. According to some embodiments, the stimulation inducer includes a wearable device, configured to be located on/near a target body region. According to some embodiments, the stimulation inducer is configured to affect a stimulation by providing physical movement, mechanical stimulation, electric stimulation, electromagnetic signal emission, temperature alteration, ultrasound stimulation or any combination thereof. According to some embodiments, the system may further include an alert module configured to provide instructions to a user regarding a change in the administration regimen of the one or more drugs or medical treatments. According to some embodiments, the system may further include a communication unit configured to deliver the alert. According to some embodiments, the alert is operable via a cloud based alert system connected to a medical device or to a drug box configured to provide instructions to a user regarding the administration regimen of the one or more drugs or medical treatments.

According to some embodiments, there is provided a method for preventing, mitigating or treating partial/complete loss of effect due to adaptation, tolerance, and/or tachyphylaxis to a drug/drugs and/or medical device administered to or used by a subject in a need thereof, or non-responsiveness to drug/drugs, maximizing therapeutic effect of drug/drugs, improving target or non-target organ/organs response to therapy. According to some embodiments, the method may include receiving a plurality of physiological or pathological parameters of the subject and/or information from the subject and/or device or other sources, applying a machine learning algorithm on the plurality of physiological or pathological parameters, and determining output parameters relating to subject-specific drug or medical regimen for facilitating improvement of drug or medical device-based therapy, wherein the output parameters include drug administration parameters, cell/tissue/organ stimulation parameters, adjuvant parameters or any combination thereof. According to some embodiments, the method may further include updating output parameters such as: drug administration and specifically-dose, time and mode; stimulation and specifically-amplitude, frequency, interval and duration; and the addition of adjuvants, based on obtained information and/or initial parameters. According to some embodiments, the method may further include determining cell/tissue/organ stimulation parameters. According to some embodiments, the method may further include updating stimulation parameters based on data being continuously learned from the user/users. According to some embodiments, the machine learning algorithm further considers personal data selected from the group consisting of: age, weight, periodic caloric intake and output, gender, ethnicity, geography, pathological history/state, temperature, metabolic rate, glucose levels, blood tests and any physiological or any pathological or physiological biomarkers or parameters that can be measured, whether directly or indirectly associated with the physiological target or with the chronic disease. According to some embodiments, at least one of the physiological or pathological parameters is obtained from a sensor. According to some embodiments, the subject drug or medical regimen is irregular. According to some embodiments, the method may further include notifying the subject regarding time, dose and/or method of administration of drug/drugs and/or adjuvant drug/drugs. According to some embodiments, the method may include notifying the subject in real time. According to some embodiments, the method may further include stimulating a tissue or an organ of the subject to evoke a reaction by a form of wearable/swallowed/implanted device. According to some embodiments, the method may further include administering drug or medical regimen to the subject. According to some embodiments, updating the stimulation parameters includes utilizing machine-learning capabilities. According to some embodiments, the machine learning capabilities include deep learning. According to some embodiments, the machine learning capabilities are configured to be operated on a set of features by receiving values thereof. According to some embodiments, the method may be used for the treatment of obesity, infectious, metabolic, endocrinology, malignant, immune-mediated, inflammatory condition, inborn error of metabolism, pain, microbiome-related disorders, neurological disease, fibrosis in any organ, any type of disease in which circadian rhythm is relevant for, including jet lag, referred to as desynchronosis or circadian dysrhythmia, disorders associated or not with an effect of circadian rhythm on the effect of drugs which are dependent of time of administration for their effect, and any type of chronic medical problem that requires therapy. According to some embodiments, the method may be used for treating any chronic disease with a drug that targets the microtubules irrespective whether there is any association of the disease with the microtubules, using any dose including sub-therapeutic dosages that have no systemic effect on the microtubules nor on the systemic immune system, and are not necessarily absorbed. According to some embodiments, the drugs can be used in combination with the chronic therapy, or as a single therapy, for all types of chronic medical conditions, for prevention or treatment of adaptation to chronic therapy, or for treatment of partial or complete loss of an effect of chronic treatments, and/or for improving the beneficial effects of therapy. According to some embodiments, where low dose colchicine (0.5 mg, 3 times a day), or any other drug which potentially target the microtubule, in any dose, may include dosages which are sub therapeutic, which do not affect systemically the microtubules nor the systemic immune system, such as a dose lower than 0.5 mg per day for colchicine, administered orally, intravenously, intradermal, intrarectal, or intranasal, and is beneficial in treatment of diabetes, insulin resistance fatty liver disease, epilepsy, pain, any chronic neurological, infectious, metabolic, inflammatory, genetic, inborn error of metabolism, endocrinology-associated, immune-mediated, or microbiome-related condition, or circadian rhythm-related condition, including jet lag, referred to as desynchronosis or circadian dysrhythmia, or malignant condition, or for diseases associated with altered glycosphingolipid metabolism, or any other metabolite metabolism, and/or for providing an organ protective effect to the heart, liver, kidney, lung, brain, nervous system, muscle, pancreas and other organs, and alleviating fibrosis in any organ, or serve as an adjuvant to other immunoprotective, anti-inflammatory, or immunomodulatory agents improving the effect of these agents. According to some embodiments, the method may include using drugs that target the glycosphingolipids or any other metabolite pathways irrespective whether the physiological or pathological states are associated with derangements of the glycosphingolipid pathway, or the metabolite pathway, for prevention of adaptation to therapy, loss of chronic effect of a drug or therapy or for an improvement of an effect of a drug. These drugs can be used in combination with the chronic therapy or as a sole therapy for any type of chronic condition.

According to some embodiments, there is provided a system for preventing, mitigating or treating partial/complete loss of effect due to adaptation, tolerance, and/or tachyphylaxis to a drug/drugs and/or medical device administered to or used by a subject in a need thereof, or non-responsiveness to drug/drugs, maximizing therapeutic effect of drug/drugs, improving target or non-target organ/organs response to therapy, the system being continuous/semi-continuous/conditional/or non-continuous closed loop molecular/cellular/tissue or any organ stimulation. According to some embodiments, the system may include receiving a plurality of physiological or pathological parameters of the subject and/or information from the subject and/or device or other sources, applying a machine learning algorithm on the plurality of physiological or pathological parameters, and determining output parameters relating to subject-specific drug or medical regimen for facilitating improvement of drug or medical device-based therapy, wherein the output parameters include drug administration parameters, cell/tissue/organ stimulation parameters, adjuvant parameters or any combination thereof. According to some embodiments, the machine learning algorithm further updating output parameters such as: drug administration and specifically-dose, time and mode; stimulation and specifically-amplitude, frequency, interval and duration; and the addition of adjuvants, based on initial parameters and or initial stimulation parameters and/or obtained information. According to some embodiments, the machine learning algorithm further considers personal data selected from the group consisting of: age, weight, periodic caloric intake and output, gender, ethnicity, geography, pathological history/state, temperature, metabolic rate, glucose levels, blood tests and any physiological or any pathological or physiological biomarkers or parameters that can be measured, whether directly or indirectly associated with the physiological target or with the chronic disease. According to some embodiments, at least one of the physiological or pathological parameters is obtained from a sensor. According to some embodiments, the subject drug or medical regimen is irregular. According to some embodiments, the system may further include a processor configured to notify the subject regarding time, dose and/or method of administration of drug/drugs and/or adjuvant drug/drugs. According to some embodiments, the system may include a processor configured to notify the subject in real time. According to some embodiments, the system may further include a processor configured to stimulate a tissue or an organ of the subject to evoke a reaction by a form of wearable/swallowed/implanted device. According to some embodiments, the system may further include a processor configured to administer drug or medical regimen to the subject. According to some embodiments, updating the stimulation parameters includes utilizing machine-learning capabilities. According to some embodiments, the machine learning capabilities include deep learning. According to some embodiments, the machine learning capabilities are configured to be operated on a set of features by receiving values thereof. According to some embodiments, the system is subject-specific; drug-specific; and/or disease-specific. According to some embodiments, the system may be used for the treatment of obesity, infectious, metabolic, endocrinology, malignant, immune-mediated, inflammatory condition, inborn error of metabolism, pain, microbiome-related disorders, neurological disease, fibrosis in any organ, any type of disease in which circadian rhythm is relevant for, including jet lag, referred to as desynchronosis or circadian dysrhythmia, disorders associated or not with an effect of circadian rhythm on the effect of drugs which are dependent of time of administration for their effect, and any type of chronic medical problem that requires therapy. According to some embodiments, the system may include using drugs that target the microtubules irrespective whether there is any association of the disease with the microtubules, using any dose including sub-therapeutic dosages that have no systemic effect on the microtubules nor on the systemic immune system, and are not necessarily absorbed. These drugs may be used in combination with the chronic therapy, or as a single therapy, for all types of chronic medical conditions, for prevention or treatment of adaptation to chronic therapy, or for treatment of partial or complete loss of an effect of chronic treatments, and/or for improving the beneficial effects of therapy. According to some embodiments, the system may include using drugs that target the glycosphingolipids or any other metabolite pathways irrespective whether the physiological or pathological states are associated with derangements of the glycosphingolipid pathway or the metabolite pathway. These drugs may be used in combination with the chronic therapy or as a single therapy for the chronic condition. According to some embodiments, where low dose colchicine, or any other drug which potentially target the microtubule, in any dose, may include dosages which are sub therapeutic, which do not affect systemically the microtubules nor the systemic immune system, such as a dose lower than 0.5 mg per day for colchicine, administered orally, intravenously, intradermal, intrarectal, or intranasal, and is beneficial in treatment of diabetes, insulin resistance fatty liver disease, epilepsy, pain, any chronic neurological, infectious, metabolic, inflammatory, genetic, inborn error of metabolism, endocrinology-associated, immune-mediated, or microbiome-related condition, or circadian rhythm-related condition, including jet lag, referred to as desynchronosis or circadian dysrhythmia, or malignant condition, or for diseases associated with altered glycosphingolipid metabolism, or any other metabolite metabolism, and/or for providing an organ protective effect to the heart, liver, kidney, lung, brain, nervous system, muscle, pancreas and other organs, and alleviating fibrosis in any organ, or serve as an adjuvant to other immunoprotective, anti-inflammatory, or immunomodulatory agents improving the effect of these agents. According to some embodiments, the system may include using drugs that target the glycosphingolipids or any other metabolite pathways irrespective whether the physiological or pathological states are associated with derangements of the glycosphingolipid pathway, or the metabolite pathway, for prevention of adaptation to therapy, loss of chronic effect of a drug or therapy or for an improvement of an effect of a drug. These drugs can be used in combination with the chronic therapy or as a sole therapy for any type of chronic condition. According to some embodiments, a closed algorithm which receives input from a subject, or groups of subjects, for determining a possible change of treatment regimen may include a possible change in dosage, mode, and/or time of administration of a chronic drug, or treatment by a medical device, for any chronic therapeutic indication. Any type of input received from the subject or groups of subjects, and assessed by the algorithm for providing an output that may improve drug or medical device-based therapy for a subject. This can be applied for any type of therapy of a medical condition requiring chronic treatment. For drugs where drug levels are important, the algorithm may change the dose and/or mode of administration within a pre-defined range, to improve responsiveness while keeping the blood levels at a therapeutic range, and/or within the effectiveness range of the chronic treatment. According to some embodiments, the processing circuitry of said update module is operated to facilitate machine-learning capabilities, wherein supervised and/or unsupervised learning is utilized. According to some embodiments, the stimulation is provided for achieving a desired physiological change and the learning machine success factor is achieving and maintaining this physiological change. According to some embodiments, the goal is improving response to drug therapy, preventing, or treating adaptation to therapy, overcoming partial or complete loss of an effect to therapy, or non-responsiveness to therapy, and improving the beneficial long-term effect of the chronic drug or any type of chronic treatment. According to some embodiments, the system may be used for improvement of treatment of obesity, infectious, metabolic, endocrinology, malignant, immune-mediated, inflammatory condition, inborn error of metabolism, pain, microbiome-related disorders, neurological disease, fibrosis in any organ, any type of disease in which circadian rhythm is relevant for, including jet lag, referred to as desynchronosis or circadian dysrhythmia, disorders associated or not with an effect of circadian rhythm on the effect of drugs which are dependent on time of administration for their effect, and/or any type of chronic medical problem that requires therapy. According to some embodiments, the output system and/or stimulation inducer are configured to affect a stimulation by providing any type of a signal to a target body part, by mechanical signal, physical movement, by electric signal, by electromagnetic signal emission, by temperature alteration, by using electrical, mechanical, ultrasound wave, or other types of direct or indirect stimuli or signals, by using various types of rate and rhythms of stimuli with various frequencies, amplitudes, durations, and intervals, in structured or random manner. According to some embodiments, the sensor may be configured to measure, any physiological or pathological parameters that can be measured whether directly or indirectly associated with the physiological target. According to some embodiments, the drug may be in the form of a pill, configured to be swallowed or transplantable and reach a target body region within the digestive track (or any other organ in the body). According to some embodiments, the stimulation inducer may include a form of a wearable device, configured to be placed/held on/near a target body region, or in other places. According to some embodiments, the stimulation inducer is configured to affect a stimulation by providing any type of a signal to a target body part, by physical movement, mechanical, electric signal, electromagnetic signal emission, temperature alteration, and/or by including mechanical, electrical, or ultrasound based, or any other type of a signal, in various types of rate and rhythms of stimuli, or any type of direct or indirect stimuli. According to some embodiments, the alert may be delivered via a cloud based alert system connected to a medical device such as an inhaler, or to a drug box that had a colored code alert for each drug instructing the subject when to take the drug and delivering a message on the use of the drug.

According to some embodiments, targeting the glycosphingolipids or any metabolite pathways can prevent or alleviate adaptation, whether or not the chronic therapy is associated directly or indirectly with an effect on the glycosphingolipid or any other body metabolite pathway, and irrespective of whether glycosphingolipids are associated with the pathogenesis of the chronic disease.

According to some embodiments, targeting the microtubules can be used as a sole therapy or as an adjuvant therapy for any chronic disease, including genetic diseases, endocrinology, inflammatory, malignant, metabolic, circadian rhythm-related, inborn error of metabolism, microbiome-associated diseases, and any chronic disease that requires treatment, including by using a dose that is lower than the therapeutic dose that has no systemic effect on the microtubules.

According to some embodiments the algorithm which provides a new treatment regimen is subject-specific, and/or disease tailored, and/or drug or any type of treatment-tailored and is based on alteration of the drug or treatment regimen, and/or the adjuvant use of drugs that target the microtubules and/or the sphingolipid pathway and/or by providing stimulation to the disease-target organ and/or to any organ in the body using a stimulation device.

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other advantages or improvements.

According to some embodiment, there are provided herein methods, schemes and regimens for drug or any type of therapy administration based on parameters updated within treatment period for personalizing parameters, increasing efficacy and overcoming personalized prolonged adaptation. Taking into consideration drug or medical device-based therapy administration in accordance or discordance with subjects' dependent factors, therapy dependent factors, circadian rhythm, or any other type of factor, which directly or indirectly affect the response to therapy.

According to some embodiments, the parameters are determined and updated using a machine learning system, which provides parameter values based on feature values received from and/or related to the user.

According to some embodiments, an algorithm-based new treatment regimen is being generated for the treatment of obesity, infectious, metabolic, endocrinology, malignant, immune-mediated, inflammatory condition, inborn error of metabolism, pain, microbiome-related disorders, neurological disease, any type of disease in which circadian rhythm is relevant for, including jet lag, referred to as desynchronosis or circadian dysrhythmia, disorders associated or not with an effect of circadian rhythm on the effect of drugs, or which are dependent of time of administration for their effect, and any type of chronic medical problem that requires therapy, will be irregular aimed at improving response rate and maximizing the effect of chronic therapies.

According to some embodiments, anti-epileptics, anti-diabetic, anti-hypertensive, painkiller, and other pharmacokinetic-dependent and non-dependent drugs, treatment regimen will provide irregularity of administered dose, administration time, and mode of administration, within the therapeutic window.

According to some embodiments, the parameters are determined and updated using a machine learning system, which provides parameter values based on feature values received from and/or related to the user.

According to some embodiments, the machine learning system is a deep learning system, in which the learning on some features is guided learning, while learning on other features is unguided learning.

According to some embodiments, the number of layers/levels of the deep machine learning depends on the number of features or on the number of associations between them.

According to some embodiments, the user updates the machine with inputs indicative of progress towards the targeted physiological effect goal, and the learning machine provides updated dose and administration time parameters based on data learned from the user and/or other users.

According to some embodiments, as used herein, the term physiological goal or target may refer to value, gradient or change in physiological measure or parameter in a desired direction. For example, the goal may be avoiding development of tolerance to long-term anti-epileptic drug use. In this case, such a goal may be avoiding tolerance without setting a specific pharmaceutical dose therapy range as a target for parameter/value change.

According to some embodiments, a user may update the machine, or the machine may receive inputs from the user and/or other users that are being used to update the algorithm in a way that enables redirecting or further defining the changes in dose, time of administration, combination therapy, mode of administration, or any other change in treatment regimen, to the user. The learning machine provides updated parameters based on data being continuously learned from other users. The data received is continuously or semi-continuously analyzed based on sub groups of subjects, including based on disease parameters, targets to be achieved, subject-related parameters such as age gender, co-morbidities, concomitant medications and other factors which are subject and/or disease and/or drug related. The data received is continuously or semi-continuously analyzed based also on the combination of disease, and on the drug.

According to some embodiments, there is provided a mobile device (e.g., phone)-based system, or any other type of an alert system, for dispensing instructions to subjects, including an update module, computationally configured to receive a plurality of feature values, and provide dose and time parameters based on information it receives from EEG, ECG, EMG, MRI, CT, PET, PET/CT, US, X-ray, DEXA, blood tests, any type of physiological or pathological biomarkers, parameters which are directly or indirectly related to the chronic disease, laboratory studies, and such.

According to some embodiments, the processing circuitry of the update module is operated to facilitate machine-learning capabilities, wherein supervised and/or unsupervised learning is utilized.

According to some embodiments, the machine learning capabilities include deep learning capabilities.

According to some embodiments, the physiological goal is avoiding development of adaptation, habituation, or tolerance to long-term drug therapy.

According to some embodiments, the machine learning success factor is maintaining physiological change.

According to some embodiments, the features of the machine learning are selected from a list including: disease type, type of drug, dose, mode of administration, side effects of the drug; microbiome-associated factors, concomitant medications; and list of subject related parameters including age, weight, gender, ethnicity, geography, pathological history/state, past/present medications, temperature, metabolic rate, glucose levels, blood tests and any physiological or pathological parameters that can be measured whether directly or indirectly associated with the physiological target; any type of biomarker which directly or indirectly associated with a disease and/or to the drug and/or to a subject or to a subgroup of subjects.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by study of the following detailed descriptions According to some embodiments, the parameters are determined and updated using a machine learning system, which provides parameter values based on feature values received from and/or related to the user.

According to some embodiments, the machine learning system is a deep learning system, in which the learning on some features is guided learning, while learning on other features is unguided learning.

According to some embodiments, the number of layers/levels of the deep machine learning depends on the number of features or on the number of associations between them.

According to some embodiments, the user updates the machine with inputs indicative of progress towards the target physiological effect goal, and the learning machine provides updated stimulation parameters based on data learned from the user and/or other users, while a different physiological goal may be given to other users with similar feature values such as race, age, gender, health conditions, concomitant medications, and so on, as well as data specific to the user, for example progress towards diabetes control, hypertension control, pain control, epilepsy, or any chronic disease.

According to some embodiments, as used herein, the term physiological goal or target may refer to value. Once the goal is achieved the stimulation may change only to maintain it, or, for example, when the user gets closer to the target value, the stimulation change, such as "slows down".

According to some embodiments, as used herein, the term physiological goal or target may refer to a gradient or change in a physiological measure/parameter in a desired direction. For example, the goal may be control of epilepsy or control of diabetes, or pain, without determining an exact value as a target for the physiological measure/parameter.

According to some embodiments, a user may update the machine, or the machine may receive inputs from the user and/or from other users which are being used to update the algorithm in a way that enable to redirect or further define the ideal dose, time, and mode of administration, and/or the best drug or drug combination to be used or any other type of treatment regimen.

According to some embodiments, a user may update the machine, or the machine may receive inputs from the user and/or from other users which are being used to update the algorithm in a way that enable to redirect or further define treatment regimen and/or defined stimuli being administered to the user following a closed-loop system.

According to some embodiments, newly generated treatment and/or regimen or stimuli further contributes to progression towards a target physiological effect goal, and the learning machine provides updated stimulation parameters based on data being continuously learned from other users. According to some embodiments, the data received is continuously or semi-continuously analyzed based on factors associated with the disease, the drug, and/or subgroups of subjects, targets of physiological levels to be achieved, as well as age, gender, concomitant diseases, concomitant medications, biomarker which may be of relevance to the treatment of disease, and others.

According to some embodiments, there is provided a system for closed loop stimulation including an update module, computationally configured to receive a plurality of feature values, and provide a new treatment regimen, and/or stimulation parameters based thereon, at least one sensor, configured to measure a physiological or pathological property, and provide a signal indicative thereof, and output device that notifies the subject when to take the medication, and at which dose, or which medications to combine, and/or use of adjuvant drugs that target the microtubules and/or glycosphingolipid pathway and/or any other metabolite pathway, and/or generates a specific type of stimuli at the organ site, or any other site of the body. These include the use of drugs that target the microtubule in a low dose that has no effect on the microtubules.

According to some embodiments the loop will include a stimulation device, including: a stimulation inducer, configured to generate a stimulation action based on stimulation parameters to affect a physiological or pathological change in a target organ or organs.

According to some embodiments the system includes a communication unit, configured to allow transfer of data to the main part of the algorithm which set up the output, and/or a signal to a stimulation device for modifying one or more treatment regimens parameters and/or use of adjuvant drugs, and/or stimulation parameters, an update module, including a processing circuitry, configured to: obtain a signal from the sensor, determine stimulation parameters based on the signal obtain from the sensor, provide an alert on the new treatment regimen and/or provide stimulation device with the determined stimulation parameters via the communication unit.

According to some embodiments, the processing circuitry of the update module is operated to facilitate machine-learning capabilities, wherein supervised and/or unsupervised learning is utilized.

According to some embodiments, the stimulation is provided for achieving a desired physiological change, and the learning machine success factor is achieving and maintaining this physiological change.

According to some embodiments, the physiological goal is prevention of adaptation or partial or complete loss of an effect to therapy of any chronic disease or chronic condition which requires therapy, such as when aiming at a lowering bodyweight, managing glucose levels, lowering blood pressure, treating cancer, treating acute or chronic pain, circadian rhythm related disorders including jet lag, treating epilepsy or any neurological disease, treating any metabolic disease, treating endocrinology disorders, treating genetic disorders, treating inborn error of metabolism, treating microbiome-associated conditions, treating any liver disease, treating all types of diabetes, treating any infectious disease including viral, such as HIV, HBV, bacterial, fungal infection, treating inflammatory or immune mediated disease.

For example, such immune-related disorders may be an autoimmune disease, graft rejection pathology, inflammatory bowel disease, non alcoholic fatty liver disease, hyperlipidemia, atherosclerosis, metabolic syndrome or any of the conditions including the same.

Examples of autoimmune disorders include, but are not limited to, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo.

The treatment described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection. According to a specifically preferred embodiment, an autoimmune disease treated by the composition disclosed herein may be any one of rheumatoid arthritis, type I diabetes, artherosclerosis, asthma, acute and chronic graft versus host disease, systemic lupus erythmatosus, scleroderma, multiple sclerosis, inflammatory bowel disease, psoriasis, uvietis, thyroiditis and immune mediated hepatitis. Embodiments of the disclosure may be applicable for the treatment of hypertension, diabetes, and the metabolic syndrome.

The metabolic syndrome is characterized by a group of metabolic risk factors in one person including: Abdominal obesity (excessive fat tissue in and around the abdomen); Atherogenic dyslipidemia (blood fat disorders—high triglycerides, low HDL cholesterol and high LDL cholesterol—that foster plaque buildups in artery walls); Elevated blood pressure; Insulin resistance or glucose intolerance; Prothrombotic state (e.g., high fibrinogen or plasminogen activator inhibitor-1 in the blood); and proinflammatory state (e.g., elevated C-reactive protein in the blood). People with the metabolic syndrome are at increased risk of coronary heart disease and other diseases related to plaque buildups in artery walls (e.g., stroke and peripheral vascular disease) and type 2 diabetes.

The above method may be applicable for prevention of adaptation to anti-cancer drugs. Malignancy, as disclosed herein, in accordance with some embodiments, may be selected from the group consisting of carcinomas, melanomas, lymphomas, myeloma, leukemia and sarcomas. Malignancies may include but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including lung, liver, breast, colon, prostate GI tract, pancreas and Kaposi). More particularly, the malignant disorder may be hepaotcellular carcinoma, colon cancer, melanoma, myeloma, acute or chronic leukemia.

The above method may be applicable for non responsiveness or prevention of adaptation to anti epileptic drugs; non responsiveness or prevention the loss of effect of pain killers; prevention of adaptation to drugs that work on the heart and blood vessels; prevention of adaptation or loss of effect of anti hypertensive medications; prevention of adaptation or loss of effect or improvement the beneficial effects of anti-diabetic drugs including insulin; sodium-glucose transporters (SGLTs) including: Canagliflozin (Invokana); Dapagliflozin (Farxiga); Empagliflozin (Jardiance); Long Acting Insulin; GLP 1 such as exenatide (Byetta) and liraglutide (Victoza), at least once a day; Lixisenatide (Adlyxin) once a day injection; Drugs that last for 7 days: Albiglutide (Tanzeum); Dulaglutide (Trulicity); Extended-release exenatide (Bydureon); DPP-4 inhibitors include medications with: Alogliptin (Nesina); Alogliptin and metformin (Kazano); Alogliptin and pioglitazone (Oseni); Linagliptin (Jentadueto); Linagliptin and metformin (Tradjenta); Saxagliptin (Ongylza); Saxagliptin and metformin (Kombiglyze); Sitagliptin (Januvia); Sitagliptin and metformin (Janumet);

The above method may be applicable prevention of adaptation or loss of effect of anti-depressant medications; prevention of adaptation or loss of effect of anti viral medications and inducing of drug-resistant mutations; Losing the effect of antibiotics and the induction of antibiotic resistance; prevention of adaptation or loss of effect of therapies for inborn error of metabolism including Gaucher disease, Fabry disease; Disorders of carbohydrate metabolism; glycogen storage disease; Disorders of amino acid metabolism: phenylketonuria, maple syrup urine disease, glutaric acidemia type 1; Urea Cycle Disorder or Urea Cycle Defects: Carbamoyl phosphate synthetase I deficiency; Disorders of organic acid metabolism (organic acidurias): alcaptonuria, 2-hydroxyglutaric acidurias; Disorders of fatty acid oxidation and mitochondrial metabolism: Medium-chain acyl-coenzyme A dehydrogenase deficiency (often shortened to MCADD); Disorders of porphyrin metabolism: acute intermittent *porphyria*; Disorders of purine or pyrimidine metabolism: Lesch-Nyhan syndrome; Disorders of steroid metabolism: lipoid congenital adrenal hyperplasia, congenital adrenal hyperplasia; Disorders of mitochondrial function: Kearns-Sayre syndrome: Disorders of peroxisomal function; Zellweger syndrome: Lysosomal storage disorders: Gaucher's disease, Niemann Pick disease; Prevention of adaptation or loss of effect of therapies of peripheral or central neurological disorders: Huntington diseases; ALS; Dementia; Alzheimer's disease; treatment of genetic diseases; treatment of any endocrine disorder.

According to some embodiments, the machine learning capabilities include deep learning capabilities.

According to some embodiments, the features of the machine learning are selected from a list including: disease-associated factors, drug-related factors, and/or subject-associated factors such as age, weight, periodic caloric intake and output, gender, ethnicity, geography, pathological history/state, temperature, metabolic rate, glucose levels, blood tests and any physiological or pathological parameters and/or biomarkers that can be measured whether directly or indirectly associated with the physiological target and with the target disease.

According to some embodiments the output of the algorithm can be in a form of a notification being delivered to the subject via a cell phone-based application, or by any other method, that instructs the subject on the dose, time, and mode of administration of a drug or on the combination of drugs to be taken, or adjuvant drugs to be taken.

According to some embodiments, the stimulation inducer is configured to affect a stimulation by providing a magnetic, mechanical, electrical, temperature-based, ultrasound based, or any other type of a signal to the target body part, by physical movement, using various types of rate and rhythms of stimuli with various frequencies, amplitudes, durations, and interval, in structured or random manner (or other types of direct or indirect stimuli).

According to some embodiments, the algorithm provides a method for prevention of adaptation to therapy, or loss of effect of therapy, or non-responsiveness to therapy, by setting up an irregularity within a specific said range that will be pre-determined for each drug or treatment based on its pharmacokinetics or efficacy.

According to some embodiments, the algorithm provides a method for prevention of adaptation to therapy, or loss of effect of therapy, or non-responsiveness to therapy, by setting up a stimulatory signal with an irregularity within a specific said range that will be pre-determined for each drug or treatment.

According to some embodiments the algorithm may include the use of an adjuvant therapy that targets the microtubule, irrespective whether the disease is associated with derangement of microtubules for prevention of adaptation to therapy, or loss of effect of therapy, or non-responsiveness to therapy, by administering the adjuvant drug that targets the microtubules in combination with the chronic therapy, and/or by setting up an irregularity within a specific said range that will be pre-determined for each drug or treatment based on its pharmacokinetics or efficacy pattern.

According to some embodiments an algorithm for drugs that target the microtubules using a low dose which has no effect on the systemic microtubules nor on the systemic immune system, and which is lower than the therapeutic window.

According to some embodiments the algorithm may include the use of an adjuvant therapy that targets the glycosphingolipid pathways, irrespective whether the disease is associated with derangement of glycosphingolipid pathway for prevention of adaptation to therapy, or loss of effect of therapy, or non-responsiveness to therapy, by administering the adjuvant drug that targets the glycosphingolipids in combination with the treatment, and/or by setting up an irregularity within a specific said range that will be pre-determined for each drug or treatment based on its pharmacokinetics or efficacy pattern.

According to some embodiments, an algorithm for drugs that target the microtubules using any dose including sub therapeutic dosages, as a sole therapy for chronic conditions.

According to some embodiments, the sensor is configured to measure, temperature, oxygen levels, blood pressure, and/or blood tests, organ activity, and/or any physiological or pathological parameters or biomarker that can be measured whether directly or indirectly-associated with the physiological target.

According to some embodiments, there is provided a stimulation device for brain, or abdominal stimulation, or any organ stimulation, whether this organ is associated with the disease-target organ or not, including a stimulation inducer, configured to generate a stimulation action based on stimulation parameters to affect a physiological change in a target region, which may be an organ, and a communication unit, configured to allow transfer of data between the stimulation device and an update module, wherein the update module includes a processing circuitry, configured to obtain a signal from at least one sensor indicative of a physiological or pathological property, determine stimulation parameters based on the signal obtain from the sensor, provide the stimulation device with the determined stimulation parameters via the communication unit.

According to some embodiments, a method for a continuous, semi-continuous, conditional, or non-continuous closed loop any organ stimulation, including providing/placing in a proximity of a target body part a stimulation device, or transplanting a stimulation device, with a stimulation inducer, providing initial stimulation parameters to the device, based on initial acquired information and a desired physiological change, providing stimulation via the stimulation inducer based on the initial stimulation parameters, obtain information from the user and/or device or other sources, and update the stimulation parameters based on the obtained information.

According to some embodiments, a method for a continuous, semi-continuous, conditional, or non-continuous closed loop for generating a new drug or medical device-based treatment regimen by providing an alert for the time, mode of administration, dose, or any other therapy-related parameter.

According to some embodiments, a method for a continuous, semi-continuous, conditional, or non-continuous closed loop for generating a new drug or medical device-based treatment regimen by adding an adjuvant therapy based on drugs which target the microtubules, or based on drugs that alter the glycosphingolipid pathway, or that can change any metabolite in the body.

According to some embodiments the pre-determined range that is set is subject-specific, and/or disease-specific, and/or drug-specific and/or adjuvant drug-specific (e.g. adjuvant drugs that target the microtubules and/or the glycosphingolipid pathway and/or any metabolite pathway, including the use of these drugs in low dosages which have no anti-inflammatory and/or microtubule effect) or any combination of these for generation of a closed-loop system. The pre-determined range may be subject to change based on the change in the status of the parameters along time.

According to some embodiments, updating the newly-generated treatment regimen based on alteration of the way the drug is being administered, and/or adding an adjuvant drug, and/or stimulation parameters, includes utilizing machine learning capabilities. According to some embodiments, the machine learning capabilities include deep learning. According to some embodiments, the machine learning capabilities are configured to be operated on a set of features by receiving values thereof. According to some embodiments, the output new regimen will be provided to the subject by a cell-phone or computer-based alert system, or any other type of an alert system and/or by a stimulation device is an implantable device. According to some embodiments, the stimulation device is configured to be swallowed by a user. According to some embodiments, the stimulation device is configured to be placed on the body of the user.

According to some embodiments, a physiological goal is an improvement in any type of disease conditions or improving health by prevention of adaptation or loss of an effect or non-responsiveness to therapy.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

Certain embodiments are associated with drugs, which are affected, by the circadian rhythm, and/or by the microbiome, and/or by the effect of circadian rhythm on the microbiome, including jet lag, referred to as desynchronosis or circadian dysrhythmia, or disorders which may be associated with an effect on drug efficacy. According to some embodiments, the algorithm may overcome the problem of drugs associated with certain patterns of administration in terms of time, which are related to their adaptation to the effect of the drug.

Certain embodiments are associated with drugs, which target the microtubules and can alleviate or treat or prevent a disease and/or adaptation to any type of treatment by targeting the physiological or pathological circadian rhythm associated with a disease state, whether or not the disease is associated with derangement of the microtubules. These include the use of these drugs in low dosages that have no effect on the systemic microtubules or on the systemic anti-inflammatory effect.

Certain embodiments are associated with drugs, which affect the glycosphingolipid pathway, or any other metabolite pathway in the body and can alleviate or treat or prevent a disease and/or adaptation to any type of treatment by targeting the physiological or pathological circadian rhythm associated with a disease state, including jet lag, referred to as desynchronosis or circadian dysrhythmia, whether or not the disease is associated with derangement of these pathways.

Certain embodiments are associated with drugs that affect the microtubules and/or glycosphingolipid pathway or any other metabolite pathway and can alleviate or treat or prevent a disease by targeting the physiological or pathological circadian rhythm associated with a disease state.

Certain embodiments are associated with drugs that target the microtubules suing any dose including dosages that are below the therapeutic range, for treatment of genetic diseases, including diseases with inborn error of metabolism such as Gaucher, and Fabry.

Certain embodiments are associated with drugs that affect the microtubules function for any type of metabolic, endocrinology, inflammatory, infectious, or malignant disease, or pain, using low dosages of these drugs that are below their therapeutic range. These can be used as a sole therapy or as an adjuvant therapy with other therapies. These can be used as part of an algorithm-based regimen for prevention of adaptation or loss of effect or non-responsiveness to therapies, or as a sole therapy.

According to some embodiments, any disease in which an association to a circadian rhythm can be treated by targeting the microtubules irrespective of whether the disease is associated with any derangement of the microtubules, including by using drugs that target the microtubules using a sub therapeutic dose that has no systemic effect on the microtubules nor on systemic immune system.

According to some embodiments, targeting the microtubules can prevent or alleviate adaptation, and improve long term response to therapy, or improve maximal effect of a drug or of a device, whether or not the disease is associated directly or indirectly with an effect on the microtubules. These include using these drugs in dosages that have no effect on the microtubules or have no anti-inflammatory effect.

According to some embodiments, targeting the glycosphingolipids or any metabolite pathways can prevent or alleviate adaptation whether or not the disease is associated directly or indirectly with an effect on the glycosphingolipid pathway or any other metabolite pathway in the body.

Colchicine inhibits mitosis which is dependent on cytoskeletal changes. Colchicine also inhibits neutrophil motility and activity, leading to a net anti-inflammatory effect. Colchicine inhibits microtubule polymerization by binding to tubulin, one of the main constituents of microtubules. Availability of tubulin is essential to mitosis, so colchicine effectively functions as a "mitotic poison" or spindle poison (Leung Y Y, Yao Hui L L, Kraus V B. *Colchicine—Update on mechanisms of action and therapeutic uses. Semin Arthritis Rheum* 2015; 45:341-50).

Colchicine is used for treatment of gout, familial Mediterranean fever, pericarditis and Behçet's disease. For gout, colchicine is an alternative for those unable to tolerate NSAIDs. At high doses, side effects (primarily gastrointestinal upset) limit its use. Colchicine is also used as an anti-inflammatory agent for long-term treatment of Behçet's disease. It appears to have some effect in relapsing polychondritis. Colchicine is also used in addition to other therapy in the treatment of pericarditis. Colchicine is used widely in the treatment of familial Mediterranean fever, in which it reduces attacks and the long-term risk of amyloidosis. (Stack J, Ryan J, McCarthy G. Colchicine: *New Insights to an Old Drug. Am J Ther* 2015; 22: e151-7; Wechalekar M D, Vinik O, Moi J H, et al. *The efficacy and safety of treatments for acute gout: results from a series of systematic literature reviews including Cochrane reviews on intraarticular glucocorticoids, colchicine, nonsteroidal antiinflammatory drugs, and interleukin*-1 inhibitors. J Rheumatol Suppl 2014; 92: 15-25).

Colchicine is used for treatment of diseases in which inflammation plays a role in the pathogenesis of. This includes atherosclerosis heart diseases, and for the prevention of postoperative complications after heart surgery. Occurrence of atrial fibrillation is reduced by a third. It is used for prevention and treatment of postpericardiotomy syndrome (Hemkens L G, Ewald H, Gloy V L, et al. *Colchicine for prevention of cardiovascular events. Cochrane Database Syst Rev* 2016:CD011047).

Colchicine can be toxic when ingested, inhaled, or absorbed in the eyes. Colchicine can cause a temporary clouding of the cornea and be absorbed into the body, causing systemic toxicity. Side effects include gastrointestinal upset and neutropenia. High doses can also damage bone marrow, lead to anemia, and cause hair loss. All of these side effects can result from hyperinhibition of mitosis. A main side effect associated with all mitotic inhibitors is peripheral neuropathy, which is a numbness or tingling in the hands and feet due to peripheral nerve damage (Rigante D, La Torraca Avallone L, et al. *The pharmacologic basis of treatment with colchicine in children with familial Mediterranean fever. Eur Rev Med Pharmacol Sci* 2006; 10: 173-8)

Long-term regimens of oral colchicine are contraindicated in subjects with advanced renal failure (including those on dialysis). About 10-20 percent of a colchicine dose is excreted unchanged by the kidneys; it is not removed by hemodialysis. Cumulative toxicity is a high probability in this clinical setting, and a severe neuromyopathy may result. The presentation includes a progressive onset of proximal weakness, elevated creatine kinase, and sensorimotor polyneuropathy. Colchicine toxicity is potentiated by the concomitant use of cholesterol-lowering drugs (statins, fibrates). This neuromuscular condition can be irreversible (even after drug discontinuation). Accompanying dementia is noted in advanced cases. It may culminate in hypercapnic respiratory failure and death. (Lu Y, Chen J, Xiao M, et al. *An overview of tubulin inhibitors that interact with the colchicine binding site. Pharm Res* 2012; 29:2943-71; Finkelstein Y, Aks S E, Hutson J R, et al. *Colchicine poisoning: the dark side of an ancient drug. Clin Toxicol* (Phila) 2010; 48:407-14; Terkeltaub R A. *Colchicine update:* 2008. *Semin Arthritis Rheum* 2009; 38:411-9; Schlesinger N. *Reassessing the safety of intravenous and compounded injectable colchicine in acute gout treatment. Expert Opin Drug Saf* 2007; 6:625-9; Wilbur K, Makowsky M *Colchicine myotoxicity: case reports and literature review. Pharmacotherapy* 2004; 24:1784-92.)

Symptoms of colchicine overdose start 2 to 24 hours after the toxic dose is ingested and include burning in the mouth and throat, fever, vomiting, diarrhea, and abdominal pain. This can cause hypovolemic shock due to extreme vascular damage and fluid loss through the gastrointestinal tract, which can be fatal. If the affected person does not recover, they may enter the multiple-system organ failure phase of colchicine overdose. This includes kidney damage, which causes low urine output and bloody urine; low white blood cell counts that can last for several days; anemia; muscular weakness; liver failure; hepatomegaly; bone marrow suppression; thrombocytopenia; and ascending paralysis leading to potentially fatal respiratory failure. Neurologic symptoms are also evident, seizures, confusion, and delirium; children may experience hallucinations. Recovery may begin within six to eight days and begins with rebound leukocytosis and alopecia as organ functions return to normal. Long-term exposure to colchicine can lead to toxicity, particularly of the bone marrow, kidney, and nerves. Effects of long-term colchicine toxicity include agranulocytosis, thrombocytopenia, low white blood cell counts, aplastic anemia, alopecia, rash, purpura, vesicular dermatitis, kidney damage, anuria, peripheral neuropathy, and myopathy (Gasparyan A Y, Ayvazyan L, Yessirkepov M, et al. *Colchicine as an anti-inflammatory and cardioprotective agent. Expert Opin Drug Metab Toxicol* 2015; 11: 1781-94; Nuki G. *Colchicine: its mechanism of action and efficacy in crystal-induced inflammation. Curr Rheumatol Rep* 2008; 10:218-27; Bhattacharyya B, Panda D, Gupta S, et al. *Anti-mitotic activity of colchicine and the structural basis for its interaction with tubulin. Med Res Rev* 2008; 28:155-83; Niel E, Scherrmann J M. *Colchicine today. Joint Bone Spine* 2006; 73:672-8; Mundy W R, Tilson H A. *Neurotoxic effects of colchicine. Neurotoxicology* 1990; 11:539-47.)

Most side effects are dose dependent, and when severe, a reduction in dosage or complete cessation of the drug may be required. However, most of the beneficial effects of colchicine are dose dependent and much of its anti inflammatory effects are lost with lower dosages. No studies using a dose less than 0.5 mg per day showed efficacy in any indication. This comes from the fact that both its anti-inflammatory effect and its effect on the microtubules are dose dependent. Colchicine in a regular dose has an effect on diabetes; however, this was achieved when given at a dose of 0.5 mg thrice a day in NIDDM subjects. (Nidorf S M, Eikelboom J W, Thompson P L. *Colchicine for secondary prevention of cardiovascular disease. Curr Atheroscler Rep* 2014; 16:391; Lange U, Schumann C, Schmidt K L. *Current aspects of colchicine therapy—classical indications and new therapeutic uses. Eur J Med Res* 2001; 6: 150-60 (Das U N; *The Journal of the Association of Physicians of India* [1993, 41(4): 213]).

Certain embodiments claim that a low dose, which is sub therapeutic, will have an effect on chronic diseases, are not mediated by the systemic anti-inflammatory effect of the drug nor by a systemic effect on the microtubules.

Certain embodiments are associated with the use of colchicines or any drug with a potential effect on the microtubules using a dose which has no effect on the microtubules nor on the immune system for exerting exert an effect organs alleviating, treating or preventing any type of infectious, metabolic, genetic, endocrinology, inflammatory, or malignant disease, microbiome-related diseases, circadian rhythm related disorders, and their use as adjuvant therapies to chronic therapies for any chronic condition.

Certain embodiments are associated with the use of colchicine or any drug which may affect the microtubules in any dose as part of an algorithm that generates by a closed loop a treatment regimen that can prevent, alleviate or overcome adaptation or loss of effect or partial of full non responsiveness to drugs or to medical device-based treatments whether or not the disease is associated with a defect in the microtubules for any type of infectious, endocrinology, genetic, inflammatory, metabolic, microbiome-associated diseases, pain, neurological diseases, microbiome-related, or circadian-rhythm related, or malignant chronic disease. These include use of these drugs in low dosages which have no effect on the microtubules.

Certain embodiments are associated with the use of colchicine or any drug which may affect the microtubules using a dose which has no effect on the microtubules nor on the immune system but will exert an effect on organs alleviating, treating or preventing fibrosis of any organ.

Certain embodiments are associated with the use of colchicine or any drug which may affect the microtubules including by low dosages which are below the therapeutic range for treatment of genetic diseases and diseases in which there is primary inborn error of metabolism leading to disruption of the glycosphingolipids such as Gaucher disease, Fabry disease, Krabbe disease, Niemann-Pick disease, Farber lipogranulomatosis disease, Tay-Sachs disease, Guillan-Barre disease, Sandhoff disease and Metachromatic leukodystrohy.

Certain embodiments are associated with the use of colchicine or any drug that may affect the microtubules including by low dosages that are below the therapeutic range for treatment of diseases in which there is secondary disruption of the glycosphingolipids such as diabetes, fatty liver disease, malignancies, and inflammatory disorders.

Certain embodiments are associated with the use of colchicine or any drug which may affect the microtubules including the use of low dosages which are below the therapeutic range, as adjuvant to other drugs used to treat diseases which are associated with primary or secondary derangement of glycosphingolipid pathways.

Certain embodiments are associated with the use of all drugs which potentially target the microtubules in a regular dose or using dosage which are below the therapeutic range, for treatment, prevention, or alleviation of any infectious, inflammatory, genetic, endocrinology-associated, metabolic, or malignant disorder, and for treatment, prevention or alleviation of any disease associated with primary or secondary derangement of glycosphingolipid or nay metabolite pathways.

These drugs can be used in a low dose which is below their therapeutic range on in a dose which is within their therapeutic range for diseases which are not related to derangements of the microtubules.

According to some embodiments, using drugs that target the microtubules including in low dosages which are below their therapeutic range can prevent or alleviate adaptation to a drug or to a medical device-related treatment, thus enabling long term effect of a drug, or maximizing the effect of the drug whether or not the disease is associated directly or indirectly with an effect on the microtubules.

According to some embodiments, drugs in addition to colchicine which target the microtubules may include: Paclitaxel is a microtubule polymer stabilizer; Docetaxel, an analog of paclitaxel, is an inhibitor of depolymerisation of microtubules by binding to stabilized microtubules; Vincristine sulfate is an inhibitor of polymerization of microtubules by binding to tubulin; Epothilone B (EPO906, Patupilone) is a paclitaxel-like microtubule-stabilizing agent; ABT-751 (E7010) binds to the colchicine site on β-tubulin and inhibits polymerization of microtubules, not a substrate for the MDR transporter and is active against cell lines resistant to vincristine, doxorubicin, and cisplatin; TRx 0237 (LMTX™) mesylate is a second-generation tau protein aggregation inhibitor for the treatment of Alzheimer's disease (AD) and frontotemporal dementia; Ixabepilone is an orally bioavailable microtubule inhibitor. It binds to tubulin and promotes tubulin polymerization and microtubule stabilization, thereby arresting cells in the G2-M phase of the cell cycle and inducing tumor cell apoptosis; Vinblastine sulfate inhibits microtubule formation and suppresses nAChR activity, used to treat certain kinds of cancer; Nocodazole is a rapidly-reversible inhibitor of microtubule polymerization, also inhibits Abl, Abl(E255K) and Abl(T315I; Cabazitaxel is a semi-synthetic derivative of a natural taxoid; Vinblastine inhibits microtubule formation and suppresses nAChR activity, used to treat certain kinds of cancer; CYT997 (Lexibulin) is a potent microtubule polymerization inhibitor; Epothilone A is a paclitaxel-like microtubule-stabilizing agent; Fosbretabulin (Combretastatin A4 Phosphate (CA4P)) Disodium is the water-soluble prodrug of Combretastatin A4 (CA4), which is a microtubule-targeting agent that binds β-tubulin; Fosbretabulin Disodium inhibits the polymerization of tubulin, and also disrupts tumor vasculature; Albendazole is a member of the benzimidazole compounds used as a drug indicated for the treatment of a variety of worm infestations; Vinflunine is a new *vinca* alkaloid uniquely fluorinated with the properties of mitotic-arresting and tubulin-interacting activity; CW069 is an allosteric, and selective inhibitor of microtubule motor protein HSET; Albendazole Oxide is a tubulin polymerization or assembly inhibitor, used for the treatment of a variety of parasitic worm infestations; Triclabendazole is a benzimidazole, it binds to tubulin impairing intracellular transport mechanisms and interferes with protein synthesis; Docetaxel, an analog of paclitaxel, is an inhibitor of depolymerisation of microtubules by binding to stabilized microtubules; Combretastatin A4 is a microtubule-targeting agent that binds β-tubulin Griseofulvin, a production from some strains of the mold *Penicillium griseofulvumam*, is able to inhibit cell mitosis by interfering with microtubule function; CK-636 is an Arp2/3 complex inhibitor of actin polymerization induced by human, fission yeast and bovine Arp2/3 complex; Vinorelbine Tartrate is a semi-synthetic *vinca* alkaloid, and inhibits mitosis through interaction with tubulin; TAI-1 is a potent and specific Hec1 inhibitor, which disrupts Hec1-Nek2 protein interaction; INH1 is a cell-permeable Hec1 inhibitor, which specifically disrupts the Hec1/Nek2 interaction; INH6 is a potent Hec1 inhibitor, which specifically disrupts the Hec1/Nek2 interaction and causes chromosome misalignment; *Vicia faba* which was shown to alter tubulin in plants.

Some embodiments refer to a computer implemented method which is subject-specific and/or disease and/or drug-specific, by a way of altering the dose and/or time and/or method of drug administration and/or combination therapy and or/or use of adjuvant drugs and/or use of stimulation to any organ and/or by using adjuvants drugs that target the microtubules and/or glycosphingolipid pathways for prevention of adaptation to chronic therapies, or as sole therapies for chronic diseases, are not expected based on the current knowledge of chronic therapies.

According to some embodiments, by using drugs that target the microtubules to treat diseases in which there is no derangement in the microtubule function and/or the use of low dose of these drugs in sub therapeutic range which has no systemic effect, is not expected based on the current knowledge to exert a beneficial effect on any chronic disease.

According to some embodiments, the target diseases may not be related to microtubule dysfunction and therefore one cannot expect an effect on microtubules to affect these diseases even when the drugs are used in a dose which is within their therapeutic range.

Using drugs that target the microtubules and/or glycosphingolipids pathways, and/or metabolite pathways, and/or modulation of circadian activity but targeting them is not obvious for prevention of, alleviation of, or treatment of adaptation, non responsiveness, or loss of chronic effect of drugs.

It is not obvious to use drugs that target the microtubules using low dosages that are below their therapeutic range and which have no effect on the systemic microtubule and/or no systemic anti-inflammatory effect and/or no systemic immune effect, for treatment of chronic diseases or for prevention of adaptation to any type of drug therapy, or for improving efficacy of chronic therapies.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
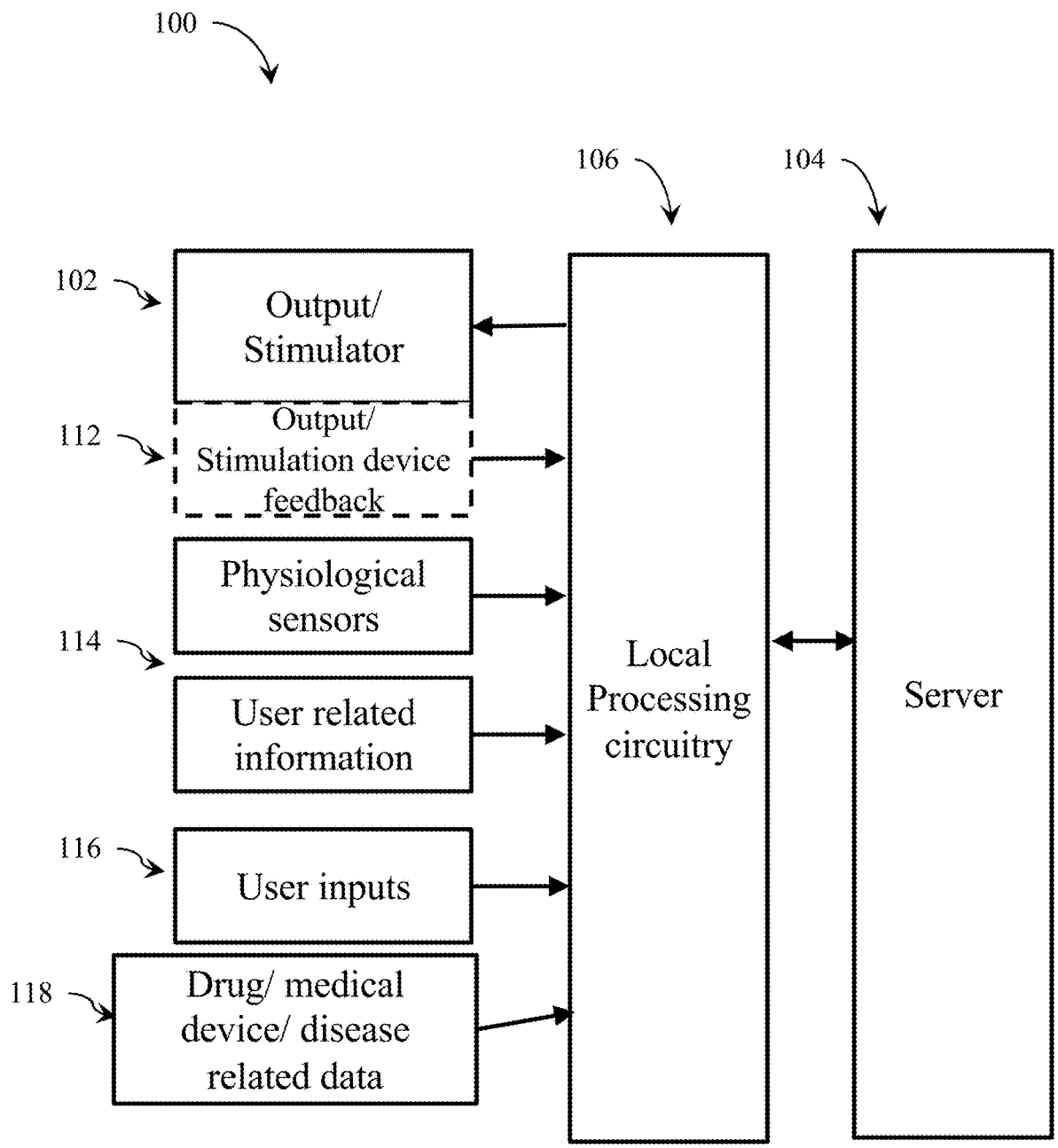
FIG. 1 schematically illustrates a functional block diagram of a system which accumulates subject-related, drug/medical device-related, and/or disease-related parameters according to some embodiments and based on the use of a pre-determined range for each drug.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiment, there are provided herein algorithms, methods, devices, and systems for preventing, mitigating or treating partial/complete loss of effect due to adaptation, tolerance, and/or tachyphylaxis to a drug/drugs and/or medical device administered to or used by a subject in a need thereof, or non-responsiveness to drug/drugs, maximizing therapeutic effect of drug/drugs, improving target or non-target organ/organs response to therapy, the method being continuous/semi-continuous/conditional/or non-continuous closed loop molecular/cellular/tissue or any other organ stimulation According to some embodiment, there are provided herein devices, systems and methods for altering the dose, and/or time of administration and/or combining different drugs and/or using adjuvant drugs for improving the long-term effect of the drug or treatment.

According to some embodiment, there are provided herein devices, systems and methods for an algorithm for combining an adjuvant drug that target the microtubules and/or the glycosphingolipid pathway and/or any metabolite pathways with any chronic drug or treatment regimen, for preventing or overcoming adaptation or loss of effect to chronic drug or medical device-based therapy. This includes the use of these adjuvant drugs in a low dose, which is below their therapeutic dose. It also includes use of regular and low dosages of drugs that target the microtubule as a single therapy for treatment of chronic diseases. Some of these embodiments relate to the use of these drugs in every chronic disease irrespective of whether the disease is associated with changes in microtubules structures or function.

According to some embodiments, any organ stimulation, wherein the output and stimulation parameters are updated within the treatment/stimulation period, for personalizing the stimulation parameters and increasing accuracy and efficacy of the output treatment regimen and/or the stimulation treatment for achieving the desired physiological goal and to prevent long-term adaptation for ensuing prolong effect of drug therapy on the target organ or physiological pathway.

According to some embodiments any type of any output treatment regimen and/or organ stimulation, wherein the stimulation parameters are updated within the treatment/stimulation period, for personalizing the stimulation characteristics to increase the accuracy and efficacy of the stimulation treatment for achieving the desired physiological goal.

According to some embodiments, the parameters are determined and updated using a machine learning system, which provides parameter values based on feature values received from and/or related to the user.

According to some embodiments, the machine learning system may be a deep learning system, in which the learning on some features is guided learning, while learning on other features is unguided learning.

According to some embodiments, the number of layers/levels of the deep machine learning depends on the number of features.

According to some embodiments, the user updates the machine with progress towards the target physiological effect goal, and the learning machine provides updated stimulation parameters based on data learned from the disease and/or the drug and/or a subject or subgroup of subject and/or disease and/or drug-related or non-related biomarkers or parameters, or combination of drugs and/or user and/or other users, that may be given to other users with similar feature values such as race, age, gender, health conditions and so on, as well as data specific to the user, for example progress towards target weight and the like.

According to some embodiments, user inputs may include any type of physiological or pathological parameters, as well as personal and environmental parameters which are relevant directly or indirectly to the drug or treatment. These parameters may be of relevance to a subject, or to a specific drug, or to a specific disease and not necessarily to all subjects.

According to some embodiments, the user may update the machine or the machine may receive inputs from the user and/or from other users which are being used to update the algorithm in a way that enable to redirect or further define the stimuli being administered to the user following a closed-loop system.

According to some embodiments, the newly generated treatment regimen for the chronic drug or drugs and/or the newly generated stimuli and/or the newly generated algorithm for adding an adjuvant drug that target the microtubules or the glycosphingolipid pathway or any metabolite pathway in the body, may further contribute to progression towards a target physiological effect goal by improving the effect of the chronic drug, or by preventing or ameliorating the adaptation or tolerance to the chronic drug, and improving non-responsiveness to chronic therapies.

The learning machine provides updated treatment regimens and/or stimulation parameters based on data being continuously learned from the user and/or other users. The data received is being continuously analyzed based subgroups of subjects including based on disease parameters, and parameters or biomarkers which are directly and non-directly associated with the disease, related in any way with the physiological levels to be achieved, as well as age, gender, concomitant diseases, concomitant medications, any type of disease related or non-related biomarkers, caloric intake, physical activity, and others.

According to some embodiment, there are provided herein devices, systems and methods for adding an adjuvant drug that target the microtubules and/or the glycosphingolipid pathway in a therapeutic or sub therapeutic dose for treatment of chronic disease.

As used herein, the terms "learning machine", "update module" and "update system" are interchangeably used, and refer to an integrated or communicatively linked component of the system, which is configured to receive input data in form of user data (such as parameter directly or indirectly associated with the chronic disease, weight, medical state, gender age and the like) in addition to features (such as measurements of directly or indirectly relevant bodily indications) and generates based thereon a stimulation parameter, a set of stimulation parameters or a series of stimulation parameters and/or forming a new treatment regimen and/or a new stimulation plan(s) based on the current inputs, historic inputs and/or preconfigured data from the user, multiple users and/or models of users.

According to some embodiments, the input data on the user along with the input received from other users on a continuous basis is being processed by the controller, which is based on a closed loop system that continuously evaluates the distance of the tested parameter from the level to be achieved or the direction and/or rate of changes in the physiological or pathological measurement/parameter, generates an improved algorithm being transformed into new output.

According to some embodiments the algorithm provides a method for prevention of long term adaptation, and prevention of tolerance, or prevention of loss of an effect to chronic treatment, with a drug or medical device, or any type of treatment, by setting up an irregularity within a specific said range that will be pre-determined for each drug, or drug combinations, based on their pharmacokinetics or pattern of efficacy.

According to some embodiments the algorithm provides a method for prevention of long term adaptation, and prevention of tolerance, or prevention of loss of an effect, to chronic treatment with a drug or device, or any type of treatment, by setting up an irregularity in the mode of drug administration, irregularity in the combination of various drugs, or irregularity in mode of administration, or any type of irregularity which is relevant to the chronic drug or drugs, or medical device-based therapies.

According to some embodiments the algorithm provides a method for prevention of long term adaptation, and prevention of tolerance, or prevention of loss of an effect to chronic treatment with a chronic drug or device or any type of chronic therapy, by setting up an irregularity in the mode of using adjuvant drugs that target the microtubules, or the glycosphingolipid pathway, or any type of body metabolite pathway. It includes the use of adjuvant drugs in dosages below their therapeutic range, their use in combination with the chronic therapy, or as a single therapy for the chronic disease.

The output can be in a form of an alert delivered to the subject via a cell phone-based application, or by any other method, which will instruct the subject on the dose, time, and mode of administration of a drug or on the combination of drugs or adjuvants to be taken.

According to some embodiments, the output can be delivered by stimulation inducer is configured to affect a stimulation by providing a mechanical, magnetic, electrical, temperature-based, ultrasound based, or any other type of a signal to the target body part or any other body part, by physical movement, using various types of rate and rhythms of stimuli with various frequencies, amplitudes, durations, and interval, in structured or random manner (or other types of direct or indirect stimuli).

Reference is now made to FIG. 1 of an output drug alert device and/or stimulation system 100, according to some embodiments. According to some embodiments, system 100 includes a drug alert output device and/or stimulator 102 or drug alert output device and/or stimulation inducer, which is configured to provide drug alert device output treatment regimen and/or stimulation to a target body part (abdominal, brain, or any other organ in the body), to achieve a desired physiological effect, optionally one feedback mechanism 112 associated with stimulator 102, configured to provide measurements of physiological indictors such as hypertension, weight, pain, diabetes control, epilepsy, temperature, pressure, impedance, and the like from the target body part or a proximity thereof, or any other disease related or non-related biomarker, or alternatively, technical information related to stimulator 102, such as battery charge level. These parameters may be related or non-directly related to the physiological target which the algorithm is aimed at improving.

According to some embodiments, system 100 may further include additional external sensors 114, for example blood tests that provide data on degree of inflammation, or for measuring blood oxidation or coming from results of blood tests or any other test and the like, which along with the information from feedback mechanism 112 are provided to a local processing circuitry 106 which is configured to control the operation of stimulator 102 based on inputs that include measurements of external or internal sensors 114, and optional feedback mechanism 112. According to some embodiments, processing circuitry 106 is further configured to obtain inputs of user related information 116 and other user inputs 118, based on which, the stimulation parameters are determined.

According to some embodiments, external sensors 114 and 118, may be a disease-related biomarker sensor, configured to provide local processing circuitry 106 with information indicative of the disease-target parameters such as weight of the user at certain times. According to some embodiments, a user may be instructed or advised to measure their disease-associated biomarker periodically, or any other parameter that may have a direct or indirect relevance to the chronic therapy, at certain times or after/at/before certain events.

According to some embodiments, processing circuitry 106 may be in communication with a remote server 104 for tapping into the computing performance thereof, and/or data of previous/other users. According to some embodiments, remote server 104 may be a cloud computer.

According to some embodiments, processing circuitry is designed for a continuous closed loop data input and output, wherein stimulation parameters are adjusted based on the input information and data.

According to some embodiments, the output and/or stimulation device may be introduced to provide an alert for a preferred drug therapy based on change in the selected drug, time or mode of administration, dose, or combination of drugs and/or the use of adjuvant drugs and/or stimulation from within the human body, for example as a capsule swallowed by the user, or a wearable or any other device placed at certain positions to affect the desired stimulation.

According to some embodiments, the output/stimulation device may be introduced to provide stimulation from within the human body, for example as a transplantable device to be placed at certain positions to affect the desired stimulation or an ingestible object (like a capsule).

Figure 2:
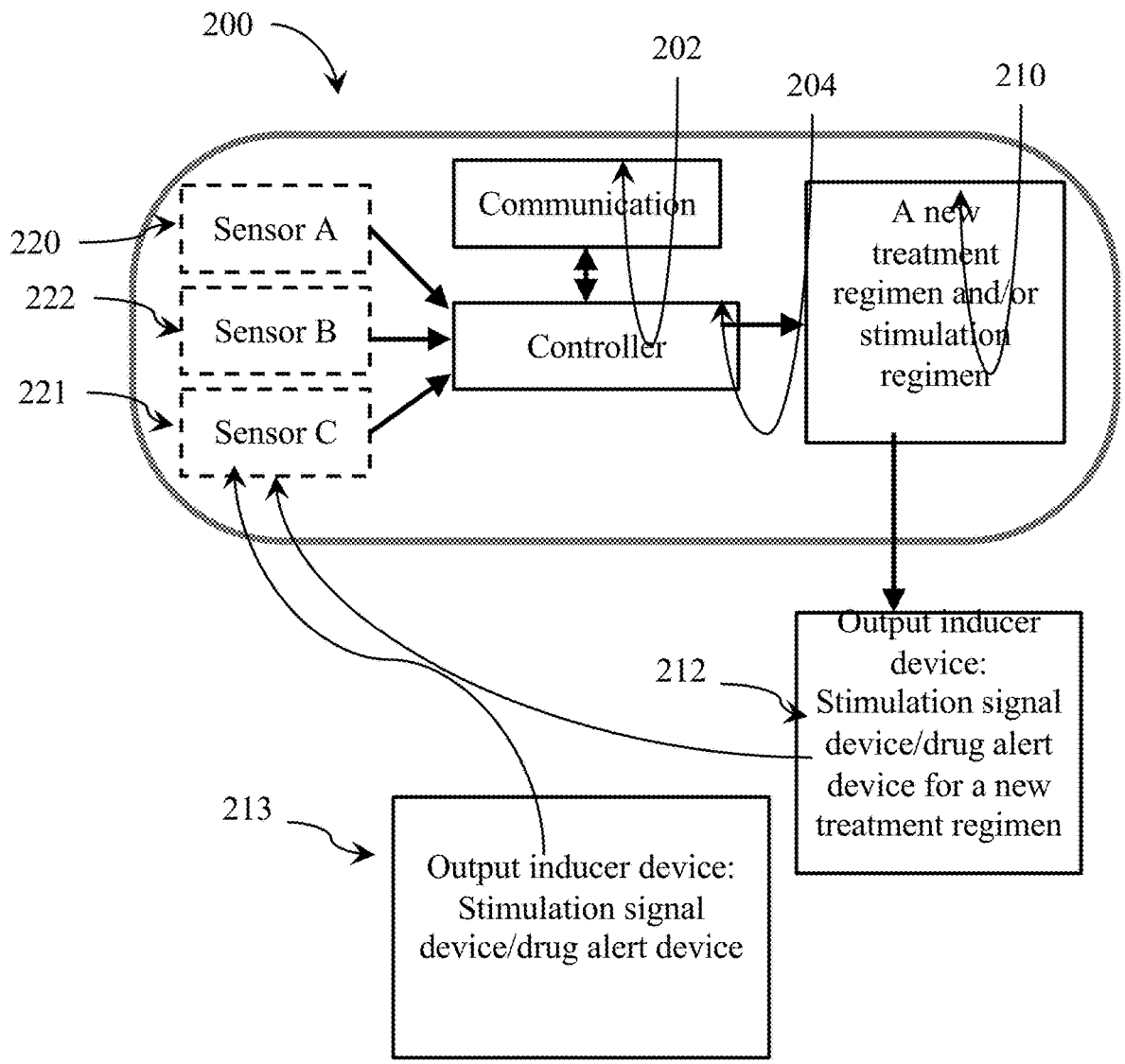
FIG. 2 schematically illustrates a functional block diagram of the closed loop-based algorithm for improving treatment to prevent target organ adaptation or loss of response to therapy according to some embodiments. The closed loop provides a method for learning and for generating a new treatment regimen and/or stimulation to be delivered to the subject.

Reference is now made to FIG. 2, which schematically illustrates a functional block diagram of a treatment regimen 200, according to some embodiments. According to some embodiments, the regimen 200 is in a form of an algorithm that creates alerts for preferred drug selection, time or mode of administration, or combination of drugs, and/or use of adjuvant drugs that target the microtubules or that target the glycosphingolipid pathway, including using a low dose which is below the therapeutic range, or the use of medical devices, and/or in a form of a pill or any other internal or external device 200, and includes several sensors 220, 222, 221 which collects data. This include subject-related data and/or drug/medical device related data, and/or disease related data using biomarkers or parameters which are related or not directly related to the disease, and/or data on pharmacokinetics of a drugs and t1/2 of a drug, and on pattern of efficacy of a treatment, configured to provide a sum of data to be used for generation of a preferred treatment regimen of a preferred stimulation that prevent adaptation to drug therapy.

The data is being analyzed by the controller via a communication device 202. An output device 212 will generate a new algorithm which in than being delivered to the subject in a form of a drug alert for altering the mode of drug use, and/or the use of adjuvant medications, and/or stimulation of target organs. The data of the effect of the output is being re-collected by the sensors 220, 221,222 and closing the learning loop.

According to some embodiments, device 200 may optionally further include sensors, such as optional sensor A 220, optional sensor B 222, and optional sensor C, in addition to a controller 204, configured to control the operation of first treatment regimen parameter or stimulation parameter inducer 210, and an output device 212, as well as several additional such output devices such as 213 to achieve a physiological change towards a physiological goal, according to drug and/or stimulation parameters that are received via communication unit 202, which is configured to be in communication with an external or internal update module/unit/circuitry for receiving the stimulation parameters, and sending thereto information from the sensors, or other operational information.

According to some embodiments, the output device for treatment and/or stimulation device may include non-transitory memory for storing therapeutic and stimulation sessions to be provided to the user. According to some embodiments, the therapeutic and stimulation device does not include memory thereon for storing stimulation session, but is rather controlled by the update-unit for changing the therapeutic and stimulation parameters whenever such a change takes place.

Figure 3:
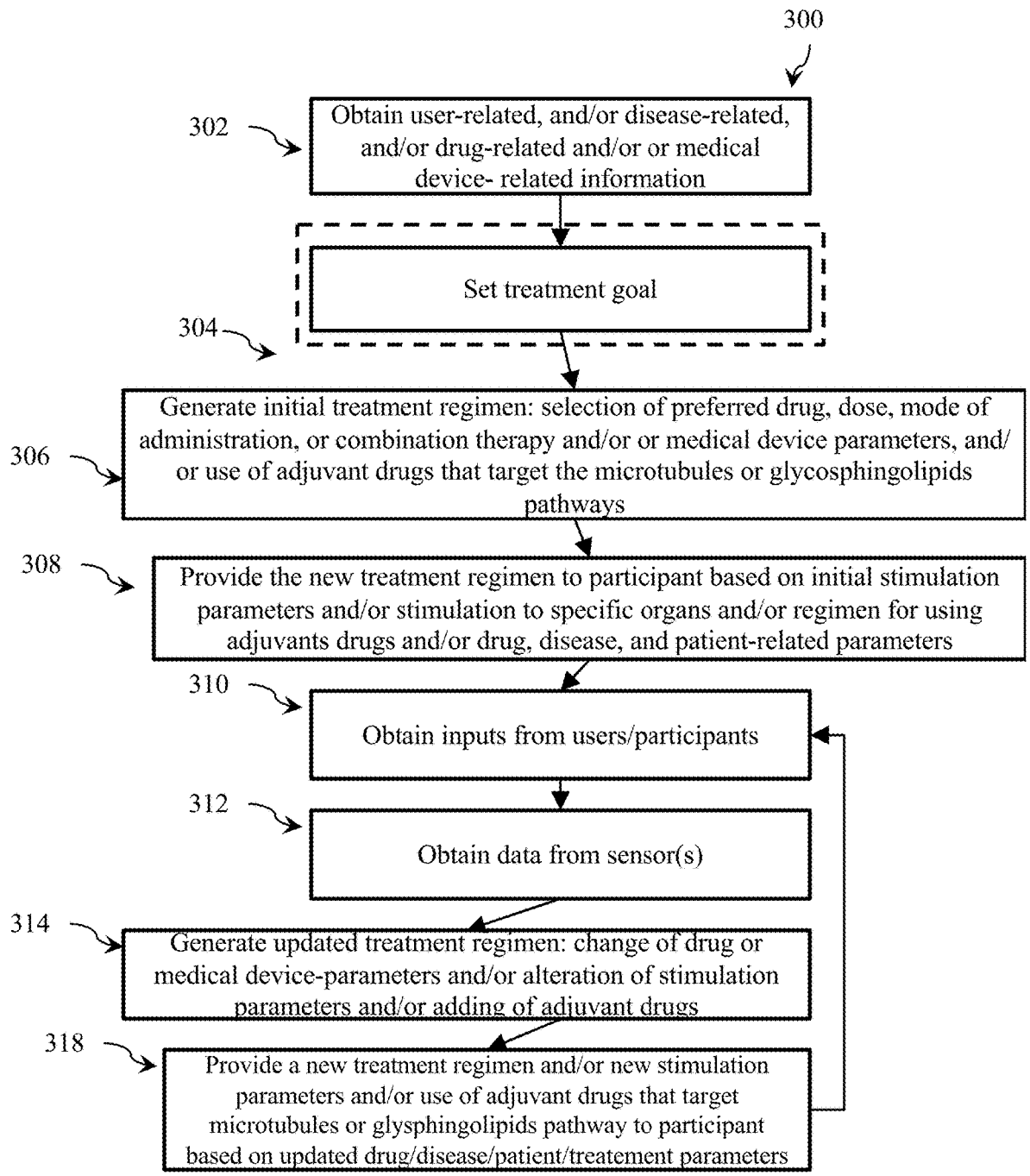
FIG. 3 schematically illustrates a method for providing updated treatment scheme using a drug, and/or combination of drugs, and/or medical device, and/or adjuvant drugs, and/or stimulation pattern using a stimulation device according to some embodiments.

Reference is now made to FIG. 3, which schematically illustrates a method 300 for providing updated parameter generation of an alert for a better drug therapy or any type of stimulation signal being generation, according to some embodiments. According to some embodiments, method 300 begins by obtaining user related information (step 302) which may be sensor measurements, or more general information such subject-related, drug-related, disease-related, biomarker-related, and/or any parameter which is directly or indirectly of relevance to the effect the chronic drug or drugs, as concomitant medications, weight, dimensions, gender, clinical history and the like or data which is specific for the drug such as pharmacokinetics, or data which is specific or of relevance to the disease, then, if there is no general goal, a drug/disease-specific regimen is being determined and an alert sent to the subjects and/or stimulation physiological goal is set (step 304) which may include a target disease related endpoint such as suppression of epilepsy, amelioration of pain, alleviation of inflammatory disease, malignancy, infection, body weight, glucose levels, blood pressure levels, improvement of function of any organ which is not well functioning, or any organ which is affected by inflammatory, infectious, genetic, or endocrinology, metabolic disease, malignant process, or any chronic medical condition that requires intervention, or a change to a positive direction of one or more of the abovementioned physiological parameters, such as control of epilepsy, reduction in weight and/or reduction in blood pressure.

Accordingly, initial output treatment regimen and/or stimulation parameters are determined (step 306) and provided to a participant (step 308). Then, input is provided to the device, which may include updated weight or other measures (step 310), or sensor data (step 312), and then updated stimulation parameters are generated accordingly (step 314) and output treatment regimens and/or stimulation is provided to the participant based on the updated parameters (step 318), and then back to step 310 for closed loop stimulation.

According to some embodiments, the system can continuously receive input from internal and external devices or from blood tests, or from subject history, from multiple subjects, which is being processed according to a deep machine learning algorithm such that relevant data from other users is being applied to the specific subject to optimize the type of treatment regimen including the use of adjuvants, and/or stimuli being generated for him. In that way a subject-specific algorithm is generated based in input from the subject and relevant data from other users or subjects.

According to some embodiments, the deep machine learning algorithm is designed to have several levels of closed loops which are built one on top of the other but also function in parallel to enable the generation of an optimize stimuli enabling reaching the physiological target.

According to some embodiments, the update system (update module) may have a dual local and network architecture, in which for example the local unit/circuitry is in real-time or short-delay loop with the stimulation device, and learn and updates the stimulation parameters without involving a higher-level computational circuitry, such as a server or a cloud computer. The update system may also include a global/network component thereto, wherein inputs may be received from multiple users, and learning from the data of the multiple users may be applied in the stimulation parameters of individual users.

Advantageously, in such a local-global architecture, the stimuli may be updated in a short/immediate closed-loop using the lower level (local) update module, wherein longer and less immediate closed-loop may update the stimuli using the higher level (global) update module.

The two-stage hierarchical architecture of the update system brought above is exemplary, and other conceptually similar architectures may apply in various embodiments.

As used herein, the term "update system" or "update module" refers to a component configured to be in wired or wireless communication with the stimulation device for set and amend stimulation parameters.

According to some embodiments, each data parameter which is received and analyzed with correlation to the stimuli generated and thus the algorithm can determine the type of data, or features, which is most relevant for a specific user/subject which correlate with the physiological target or desired physiological change. This input parameter may not be identical to all users/subjects and may not be identical for the same user/subject regarding different physiological targets, objectives or improvements.

According to some embodiments, the stimulation characteristics may change over time even for the same user with the same desired physiological change, and even if there is a positive physiological change. Such changes in stimulation characteristics may be done for avoiding habituation of the user to the stimulation, and maintaining a positive physiological change.

Figure 4:
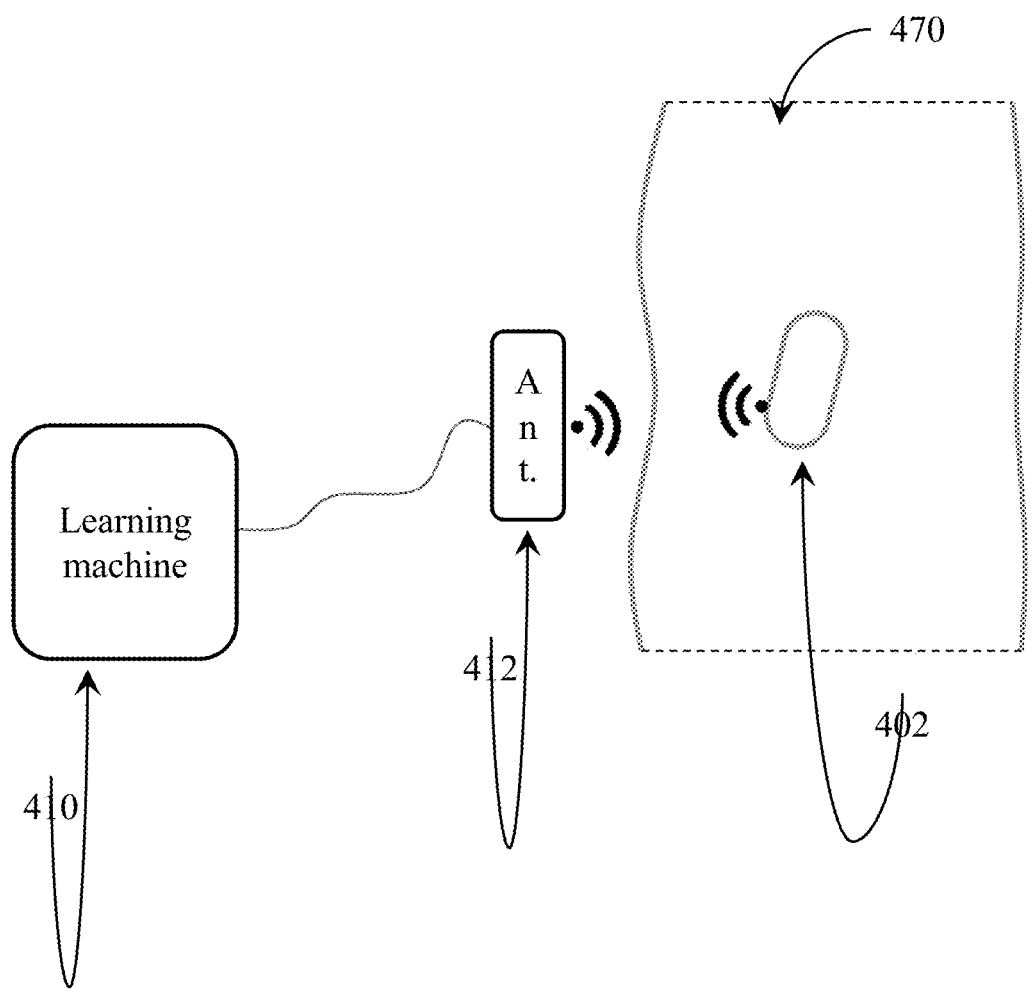
FIG. 4 schematically illustrates a method for providing internal or external stimulation to the brain or to any target organ for prevention of adaptation of loss of a chronic effect of a drug or any other type of therapy.

Reference is now made to FIG. 4, which schematically illustrates an internal or external brain, abdominal or any other organ stimulation system 400, according to some embodiments. According to some embodiments, system 400 includes a stimulation device 402, configured to be inserted to be introduced to a target area of a subject 470, to induce stimulation thereto, According to some embodiments, stimulation device is in communication with an update module, such as learning machine 410 via wireless communication link, such as through antenna 412, for sending sensor information from stimulation device 402 to learning machine 410, and receiving updated stimulation parameters therefrom, to adjust the stimulation and achieve desired results towards reaching the target goal of a physiological feature.

According to some embodiments, stimulation techniques may include mechanical, magnetic, electric, electromagnetic, ultrasound, thermal or the like. According to some embodiments, changes in stimulation characteristics may include variations or changes in stimulation patterns (repetitions), frequency, intensity, and duration. According to some embodiments, stimulation may be provided continuously or intermittently with On/Off time periods, and the duration of the time periods and/or the ration between them may be changed in either a structured manner, randomly or semi-randomly.

According to some embodiments the stimulation device is configured to be placed at a desired position on the body of the participant to induce stimulation thereto, for example by being fastened using a strap/belt or via any type of a device.

According to some embodiments, stimulation device is in communication with an update module, such as learning machine, for updating stimulation parameters/characteristics. According to some embodiments, the communication may be wireless.

According to some embodiments, both external and internal devices can be used for data collection and input of data from various organs and/or for the generation of the stimuli required for achieving a target physiological goal. The closed loop system is continuously or semi continuously receiving data from internal and external measured parameters from one or many users, and are continuously being processed by the controller for generating a new stimuli to be administered to the user via an internal or external device.

Figure 5:
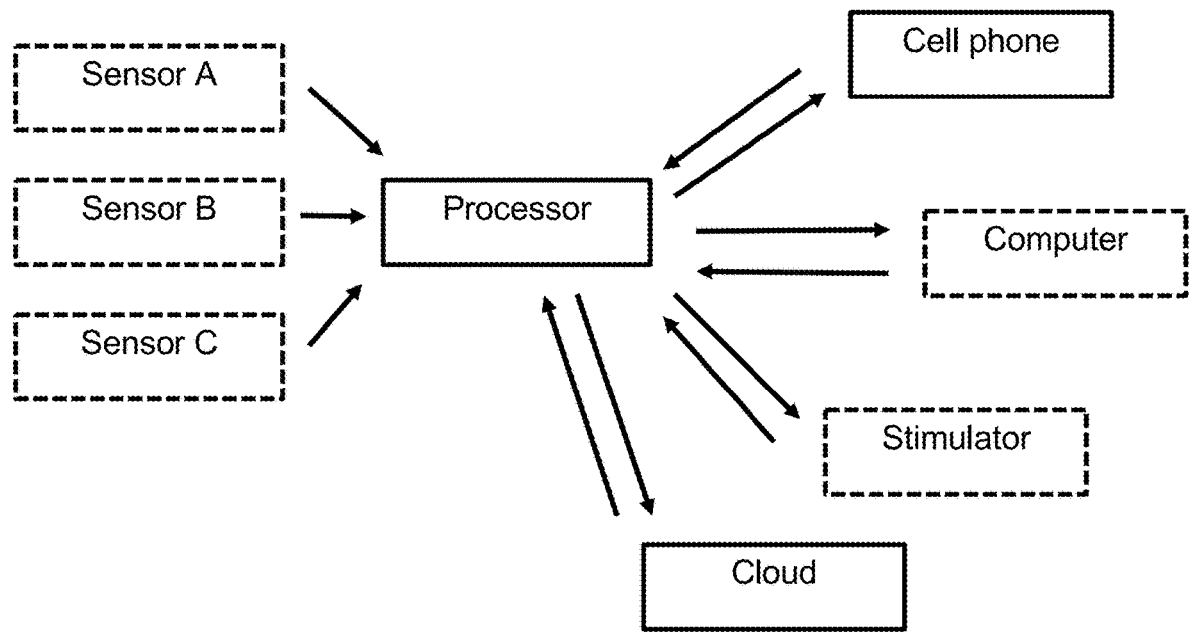
FIG. 5 schematically illustrates a functional block diagram of the closed loop system FIG. 6 schematically illustrates a method for providing treatment through the closed loop system.

Reference is now made to FIG. 5, which schematically illustrates a functional block diagram of the closed loop system. Where optional sensors convey data to the processor that both conveys and is fed data by a cell phone, a cloud and possibly a computer and/or a stimulator device.

According to some embodiments, the update-unit/learning-machine is updated upon changes in the measured information, or for example if the change is greater that a certain percentage of the previous value, or if the values reach a predetermined threshold, or any combination of the above.

Disclosed herein is an example of the use of a closed loop continuously learning algorithm for prevention of adaptation for drug therapy.

The target treatment is blood pressure of 140/80 mm Hg.

The physiological target: of reaching a blood pressure of 130/80 mm Hg.

The therapeutic drug alert and/or stimulation device (internal or external device) receives data from the sensors (internal and external), indicative of blood pressure, body weight, pulse, and breathing, skin conductivity along blood tests which are of relevance or irrelevant to blood pressure.

The input data is processed in correlation with the physiological target to assess whether an improvement was achieved, and to what extent. If no improvement towards the target was achieved a new drug therapeutic regimen and/or stimuli is being generated. If a positive step towards the target blood pressure was achieved the controller will then divide each type of drug range (including the type of drug, dose, mode of administration, time of administration, or drug combination, or use of adjuvant drugs that target the microtubules, or the glycosphingolipid pathway, or any other metabolite pathway) and/or the selected stimuli (electrical, mechanical, magnetic, ultrasound) into 100 percentiles that determines the percentile for each of the components of the drug range (such as time and dose being administered within a pre-determined range) and/or stimuli (such as rate of stimuli, rhythm, power, frequency, amplitude and temperature or others or any combination thereof) and which order of administration or alternating between them which was the most efficient in contributing to the achievement of the physiological change, such as blood pressure. Based on that analysis, a new therapeutic regimen and/or stimuli are generated. In general, the machine learning computer implemented method may require a plurality of blood pressure samples for learning the user and providing effective stimulations.

The output and/or stimulation parameters update mechanism/algorithm is configured to continuously narrow the range or change the order by which the stimuli are being administered, to be targeted on the most effective stimulation characteristics for the specific user.

The stimulation characteristics/parameters update mechanism/algorithm is configured to learn from indications/measurements (measured parameters) which may not be directly related to the chronic disease or to the chronic drug therapy. These include for example blood tests of electrolytes, blood oxygen or any blood test or other test which is of relevance or is irrelevant to blood pressure.

According to some embodiments, the algorithm operated in the update module may take into consideration outliers from the plurality of users, to which the learnings of the general users may not fit, and develop new models of treatment (new decision structures) for such outliers.

The algorithm, per one subject, may be developed based on big data analysis generated from multiple subjects. It is noted that the new treatment regimen and/or the new stimuli regimen generated by the big data can be further analyzed by type of disease, type of drug, and subject related factors such as age, gender, body weight, delta of change in the target physiological parameter (e.g. weight) over time, concomitant diseases, geographic location, weather conditions, concomitant medications, and other disease and/or subject and/or drug-parameters, it may not be identical per all subjects, and is only a contributing level of data to the deep machine learning algorithm which generated a subject-specific algorithm.

Figure 6:
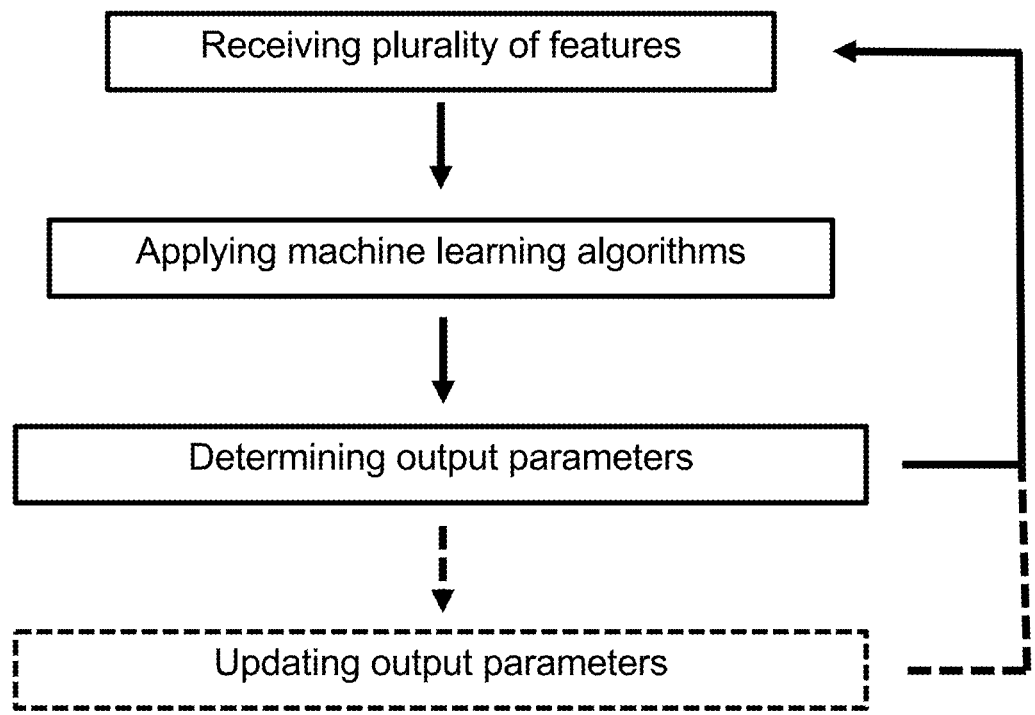

Reference is now made to FIG. 6, which schematically illustrates a method for providing treatment through the closed loop system. Initially, a plurality of features is received, on which are applied machine learning algorithms. Output parameters are then determined and added as additional feature plurality or used to update the output parameters which are then added as additional feature plurality.

According to some embodiments, the algorithm may change over time per each subject, such that a decrease in blood pressure of 180/100 may not require the same regimen stimuli as that of decreasing from 160/100 to 140/80. As the algorithm is continuously learning, it will change itself continuously based on both the data being accumulated by the big data and from each subject.

For example, a stimulus that is being generated by a belt on the brain and/or over the abdomen that can generates several types of stimuli (electrical, mechanical, vibration and heat) with three stimulation parameters:

Frequency, intermittency (intervals between On and Off periods), and power/temperature.

According to some embodiments, using drugs which affect the microtubules for diseases that are not associated with any type of microtubule dysfunction, and/or using these drugs in dosages which are lower than their therapeutic range, which have no systemic effect on the microtubule nor on the systemic immune system, for prevention of loss of an effect of drugs or treatment in subjects with any type of infectious, malignant, inflammatory, metabolic chronic disease, or in subjects with pain or any other type of chronic illness. These drugs can be administered as adjuvant to the drug therapy, or medical device treatment, or can be used as a sole therapy in a therapeutic range dose, and/or using any dose which is not within the therapeutic range.

For example, if a subject suffers from epilepsy and lost the effect of treatment, he can use one of the followings or any combination of the following for prevention of loss of the effect of the drugs, or for treatment of loss of the effect of the drugs, or for maximizing the effect of the drugs:

a. Use a subject-specific algorithm that determines an irregularity of the mode, dose, time of administration, and/or change of drug combination therapy, or any other type of irregularity, which is associated with the treatment.

b. Use a stimulatory device that can be put on the brain or on any other organ that delivers any type of mechanical, electrical, ultrasound-based, temperature-based, or any other type of stimuli in addition to the chronic drug regimen.

c. Add a drug which targets the microtubules using a dose which is within the therapeutic range as an adjuvant to his treatment regimen.

d. Use a drug which targets the microtubule using a dose which is within its therapeutic range as a sole therapy for his disease.

e. Add a drug which targets the microtubules using a dose which is lower and is below the therapeutic range as an adjuvant to his treatment regimen.

f. Use a drug which targets the microtubule using a dose which much lower and is below its therapeutic range as a sole therapy for his disease.

g. Add a drug which targets the glycosphingolipid or any other metabolite pathway in a dose which is within the therapeutic range as an adjuvant to his treatment regimen.

h. Use a drug which targets the glycosphingolipid or any other metabolite pathway using a dose which is within its therapeutic range as a sole therapy for his disease.

i. Add a drug which targets the glycosphingolipid or any other metabolite pathway using a dose which is lower and outside of therapeutic range as an adjuvant to his treatment regimen.

j. Use a drug which targets the glycosphingolipid or any other metabolite pathway using a dose which is lower and outside of its therapeutic range as a sole therapy for his disease.

k. Use of an algorithm of any combination of the above.

As used herein, the terms "electronic device", "mobile electronic device" and "mobile device" may be interchangeably used, and may refer to electronic/computerized devices with communication capabilities, processing circuitry and a non-tangible memory. The device may support wired and/or wireless communication channels. The device may be wearable or handheld, the device may be mobile, and the device may be one or more of: a cellphone, a wearable device such as a smartwatch, smart wrist-band, smart glass and the like, a personal computer, a laptop, a PDA, a tablet or the like.

According to some embodiments, the disclosure includes a system, a computer implemented method, and/or a computer program product. The computer program product may include a computer readable storage medium (or media) having computer readable program instructions thereon for causing a processor to carry out aspects of the present disclosure.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, "cloud-based" or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Example 1

Prevention of Adaptation and/or Improving Efficacy of Chronic Drug Therapy by an Algorithm-Based Irregularity of Drug Administration
Mice: 24 C57 Bl mice, 12 weeks old, n=4/group
All animals received daily low dose CONA 300 μg/mouse daily for 10 days
Dexamethasone daily 50 mg/kg per day

| Group | Treatment | Day 1 | Day 2 | Day 3 | Day 4 | Day 5 | Day 8 | Day 9 | Day 10 |
|---|---|---|---|---|---|---|---|---|---|
| A | PBS | 8AM | 8AM | 8AM | 8AM | 8AM | 8AM | 8AM | 8AM |
| B | Dexamethasone | 8AM | 8AM | 8AM | 8AM | 8AM | 8AM | 8AM | 8AM |
| C | Dexamethasone | 8 AM | 12PM | 17PM | 12PM | 8 PM | 12PM | 16PM | 8AM |

ALT serum levels were monitored as follows

| | Day | | |
|---|---|---|---|
| Group | 2 | 5 | 10 |
| | ALT serum level | | |
| A | 5516.75 | 6813.5 | 7892.5 |
| B | 644.25 | 978.75 | 1210.25 |
| C | 747 | 842.5 | 876.75 |

These data show that irregularity of drug administration low alt SERUM during the entire treatment and thus significantly improves the efficacy of the anti-inflammatory drug as compared to a regular treatment regimen.

Example 2

Prevention of Adaptation and/or Improving Response to Chronic Drug Therapy that Alters the Microbiome by an Algorithm-Based Irregular Drug Administration
Mice: 24 C57 Bl mice, 12 weeks old n=4/group
All animals received daily low dose CONA 300 μg/mouse 3 times per week for 10 days
Travelan (an anti LPS antibody which works on the gut microbiome) daily 50 mg/kg per day.
Travelan is an anti LPS antibody which works on the gut microbiome.

| Group | Treatment | Day 1 | Day 2 | Day 3 | Day 4 | Day 5 | Day 8 | Day 9 | Day 10 |
|---|---|---|---|---|---|---|---|---|---|
| A | PBS | 8AM | 8AM | 8AM | 8AM | 8AM | 8AM | 8AM | 8AM |
| D | Travelan | 8AM | 8AM | 8AM | 8AM | 8AM | 8AM | 8AM | 8AM |
| E | Travelan | 8AM | 12PM | 17PM | 12PM | 8PM | 12PM | 16PM | 8AM |

ALT serum levels were as follows

| Group | Day 2 | 5 ALT serum level | 10 |
|---|---|---|---|
| A | 4899.75 | 5703.5 | 7183.75 |
| D | 1026.5 | 1489.75 | 1966.5 |
| E | 917.5 | 1250.5 | 1337.25 |

This example shows that using an irregular treatment regimen provides a better therapeutic effect.

Example 3

Prevention of Adaptation and/or Loss of an Effect and/or Non-Responsiveness Using a Subject-Specific Algorithm for Treatment of Hypertension The subject is connected to a device that measures its hypertension as the endpoint for the algorithm. The algorithm is based on an input of several parameters, including for example pulse, breathing, and skin conductivity, which are measured continuously or during several periods per day. Data which related to the drug, and/or to combination therapy, and to the subject's genetic and phenotypic background, including environmental factors is being collected.

The algorithm is set up to receive data regarding dose, time of administration, and mode of administration of the drug or treatment.

The algorithm provides an output that alters in a random subject-specific way, the dose, mode of therapy and time of therapy, as well as selection of preferred drug or drug combinations or combinations with devices that reduce hypertension.

The algorithm also provides an output that produces an internal or external stimulation output to the brain or the kidney, or the abdomen, to prevent adaptation to treatment.

The algorithm also provides an output of a new treatment regimen that determines the ideal adjuvant therapy by using drugs that target the microtubules or the glycosphingolipids pathway to prevent adaptation or loss of effect or non-responsiveness to treatment.

Example 4

A Subject-Specific Algorithm-Based Therapy for Prevention of Adaptation or Loss of Effect or Partial or Non-Responsiveness to Treatment of Diabetes The subject measures his HBA1C monthly and fasting blood glucose daily as the endpoint for the algorithm. The algorithm is based on an input of several additional parameters such as GLP1 and adiponectin levels, drug-associated parameters, as well as environmental factors.

The algorithm is set up to receive data on the dose, time of administration, and mode of administration of a or treatment for diabetes.

The algorithm provides an output that alters in a subject-specific random way, the dose, mode of therapy and time of therapy, as well as selection of preferred drug or drug combination or combination with devices that control the blood sugar over a long time. The algorithm is expected to change based on the moving target HBA1C, as well as along the time of treatment.

A separate algorithm provides an output that produces an internal or external stimulation output to the brain or to the abdomen to prevent adaptation to treatment.

The algorithm provides an output of a new treatment regimen that determines the ideal adjuvant therapy by using drugs that target the microtubules or the glycosphingolipids pathway to prevent adaptation or loss of effect or non-responsiveness to treatment. These drugs can be used in a low dose which is outside of their therapeutic window.

Example 5

A Subject-Specific Algorithm for Prevention of Adaptation, Overcoming Loss or Non-Responsiveness to Chronic Therapy of Inflammatory and Immune-Mediated Disorders A subject with rheumatoid arthritis who is treated once daily with anti-TNF based therapy. The subject measures his arthritis score monthly as the endpoint for the algorithm. The algorithm is based on an input of several additional parameters such as ESR and CRP levels.

The algorithm is set up to receive data on the dose, time of administration, and mode of administration of a or treatment for disease.

The algorithm provides of a new treatment regimen of an output that alters in a subject-specific random way, however, the dose, and time of therapy, as well as selection of preferred drug combination over a long time. The algorithm is expected to change along the time of treatment once an escape or tolerance phenomenon occurs.

A separate algorithm provides an output that produces an internal or external stimulation output to the brain or to the abdomen or to the joints to prevent adaptation or loss of an effect to treatment.

The algorithm can provide an output that determines the ideal adjuvant therapy by using drugs that target the microtubules and/or the glycosphingolipids pathway to prevent adaptation or loss of effect or non-responsiveness to treatment. These drugs can be used in a low dose which is outside of their therapeutic window.

Example 6

An Algorithm for Improving the Response in Treatment of Malignant Diseases

For adenocarcinoma of the lung a combination of drugs usually is given in a series of treatments over a period of weeks or months, with breaks in between. Targeted therapy drugs are often used in combination with chemotherapy drugs and include any of the followings: Afatinib (Gilotrif); Bevacizumab (Avastin); Ceritinib (Zykadia); Crizotinib (Xalkori); Erlotinib (Tarceva); Nivolumab (Opdivo); Ramucirumab (Cyramza). The subject is being followed by any blood biomarker or for tumor volume based on imaging based on the preferred algorithm that can determine the dose, time of administration, and mode of administration of the drugs. The algorithm provides an output that will alter in a subject-specific random way, the dose, and time of therapy, as well as selection of preferred drug combination over a long time. The algorithm is expected to change along the time of treatment once an escape or tolerance phenomenon occurs.

A separate algorithm provides of a new treatment regimen of an output that produces an internal or external stimulation output to the brain or over the lung tumor area to prevent adaptation to treatment.

The algorithm can also provide an output that determines the ideal adjuvant therapy by using drugs that target the microtubules or the glycosphingolipids pathway to prevent adaptation or loss of effect or non-responsiveness to treatment. These drugs can be used in a low dose which is outside of their therapeutic window.

Example 7

A Subject-Specific Algorithm for Prevention of Tolerance and/or Improving Responsiveness to Therapy for Epilepsy The subject is connected to an EEG device that measures its degree of brain electrical disturbance as an endpoint for the algorithm. The algorithm is based on an input of several parameters, which may be of relevant or are irrelevant to his epileptic condition.

The algorithm is set up to receive data on the dose, time of administration, and mode of administration of his treatment.

The algorithm provides of a new treatment regimen of an output that alters is a random way, however, subject-specific, the dose, mode of therapy and time of therapy, as well as selection of preferred drug or drug combination.

The algorithm provides an output that produces an internal or external stimulation output to the brain to prevent adaptation to treatment.

The algorithm can also provide an output that determines the ideal adjuvant therapy by using drugs that target the microtubules or the glycosphingolipids pathway to prevent adaptation or loss of effect or non-responsiveness to treatment. These drugs can be used in a low dose which is outside of their therapeutic window.

Example 8: Using Drugs that Target the Microtubules in a Sub Therapeutic Low Dose Lack of an effect of low dose colchicine (0.5 mg, 3 times a day) as anti-inflammatory agent, while showing beneficial effect of low dose colchicine in diabetes and fatty liver disease.
  Mice: C57Bl/6 mice, 11-12 weeks old
  Duration: Mice will be administered once Colchicine six hours before ConA
  Sacrifice: 14 hours after ConA injection.

| Group | Treatment per mouse | Administration |
|---|---|---|
| A N = 3 | Control: saline | Gavage 300 μl |
| B N = 3 | Colchicine 0.05 μg/kg = 50 ng/kg = 1.25 ng/m | " |
| C N = 3 | Colchicine 0.005 μg/kg = 5 ng/kg = 0.125 ng/m | " |

Figure 7:
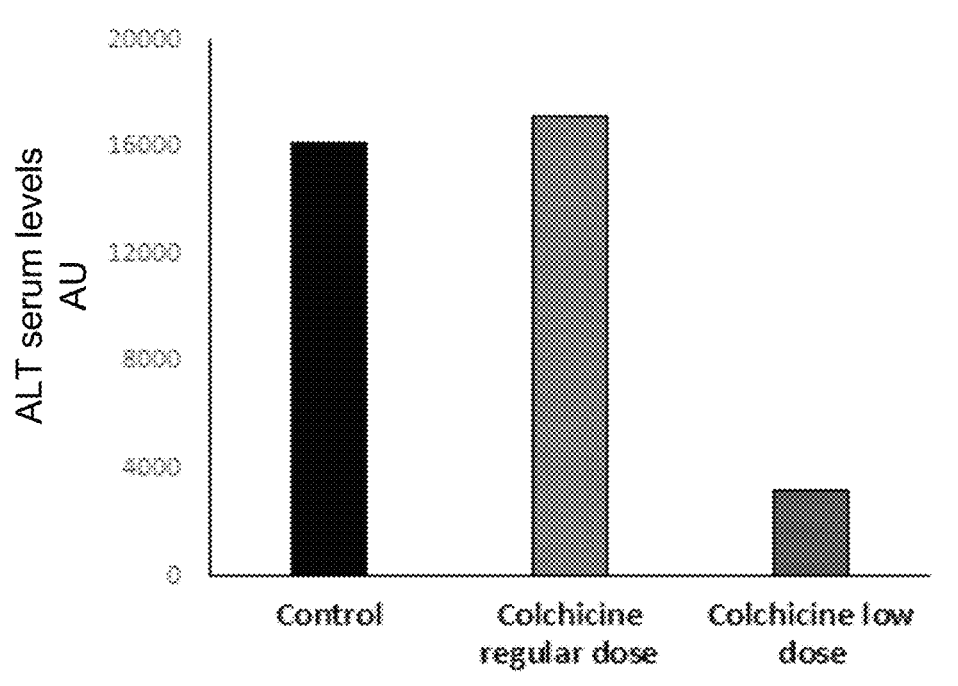
FIG. 7 shows the ALT serum levels (arbitrary units) obtained in mice left untreated, treated with a high dose Colchicine (0.05 μg/kg) or a low dose Colchicine (0.005 μg/kg).

Experiment Protocol:
  Day 1: Administer all compounds by gavage 300 ul: saline or Colchicine
  After 6 hours give Con A by injection IV 500 μg/mouse=20 mg/kg=200 ml
  Day 2: On the next day: sacrifice all mice
  Take blood for serum ALT
The results of this experiments are given in the table below and in FIG. 7.

| | Dilution | ALT | Average |
|---|---|---|---|
| Control | 1/40 | 12440 | |
| | 1/40 | 22840 | |
| | 1/40 | 13239 | 16173 |
| Regular dose | 1/40 | 18946 | |
| | 1/40 | 19427 | |
| | 1/40 | 13029 | 17134 |
| Low dose | 1/40 | 2978 | |
| | 1/40 | 1948 | |
| | 1/40 | 4728 | 3218 |

This example shows that a new treatment regimen utilizing a sub therapeutic effect of drugs that target the microtubules (a dose that has no effect on the microtubules or has any anti-inflammatory effect) an effect on chronic disease, diabetes, and fatty liver, can be achieved.

Example 9: An Algorithm for Improving Effect of Drugs and for Prevention of Loss of an Effect and/or of Adaptation to Therapy Using colchicine as an adjuvant to other drugs for prevention of adaptation to the drug and for improving efficacy.

Adding low dose colchicine to standard of care therapy in subjects with diabetes, epilepsy, cancer, or immune mediated disorder that lost the effect of chronic therapy that they receive.

Subjects are monitored using the accepted disease endpoints using a combination of colchicine administered in a low dose or in a standard dose, for a few months in subjects who lost the effect of a chronic medication.

The algorithm provides of a new treatment regimen of adding low dose of drugs that target the microtubules for prevention of adaptation and improving responsiveness to chronic therapies.
Mice: 18 C57Bl/6 mice, 11-12 weeks old
Duration: Mice will be administered once Colchicine with or without ambroxol or anti CD3 six hours before ConA
Sacrifice: 14 hours after ConA injection.

| Group | Treatment (per mouse) | administration |
|---|---|---|
| A N = 3 | Cont, saline (350 μl) | PO |
| B N = 3 | Colchicine 0.01 mg//kg | PO |
| C N = 3 | Colchicine 0.01 mg//kg with Ambroxol 1.4 mg | PO |
| D N = 3 | Colchicine 0.01 mg//kg with Anti CD3 20 microgram (μg) | PO |
| E N = 3 | Ambroxol 1.4 mg | PO |
| F N = 3 | Anti CD3 20 microgram (μg) | PO |

Experiment Protocol:
  Administer orally all compounds: 350 μl per mouse by gavage
  Con A 500 μg/mouse=20 mg/kg 100 μl/mouse IV
  On the next day sacrifice all mice.
  Follow up ALT levels
Results

| | ALT (IU) |
|---|---|
| Control | 9845 |
| anti CD3 20 microgram | 7549 |

-continued

| | ALT (IU) |
|---|---|
| Colchicine low dose 0.01 mg/kg + anti CD3 | 2874 |

| | Dilution | ALT | Average |
|---|---|---|---|
| Control | 1/40 | 10268 | |
| | 1/40 | 9396 | |
| | 1/40 | 9871 | 9845 |
| CD3 | 1/40 | 6921 | |
| | 1/40 | 8847 | |
| | 1/40 | 6879 | 7549 |
| CD3 + Colchicine | 1/40 | 2678 | |
| | 1/40 | 4173 | |
| | 1/40 | 1771 | 2874 |

| | ALT (IU) |
|---|---|
| Control | 6068 |
| Ambroxol 1.4 mg | 4243 |
| Colchicine low dose 0.01 mg/kg + Ambroxol | 1804 |

| | Dilution | ALT | Average |
|---|---|---|---|
| Control | 1/40 | 7521 | |
| | 1/40 | 6288 | |
| | 1/40 | 4395 | 6068 |
| Ambroxol | 1/40 | 3683 | |
| | 1/40 | 4187 | |
| | 1/40 | 4859 | 4243 |
| Ambroxol + Colchicine | 1/40 | 1852 | |
| | 1/40 | 1927 | |
| | 1/40 | 1633 | 1804 |

Figure 8:
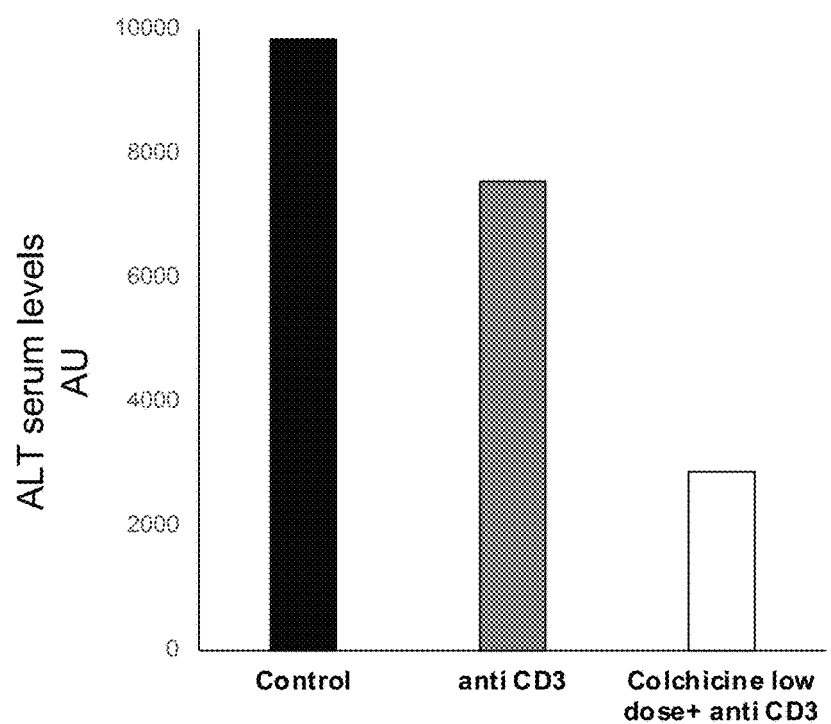
FIG. 8 shows the ALT serum levels (arbitrary units) obtained in mice left untreated, treated with Ambroxol alone or with ambroxol in combination with a low dose Colchicine.
Figure 9:
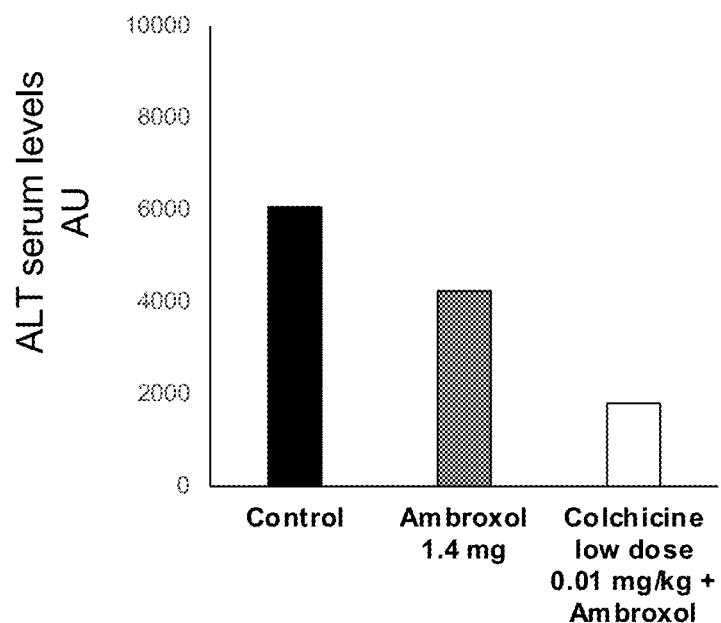
FIG. 9 shows the ALT serum levels (arbitrary units) obtained in mice left untreated, treated with CD3 alone or with CD3 in combination with a low dose Colchicine.

As seen from the above tables as well as from FIG. 8 and FIG. 9 a low dose colchicine can serve as a potent adjuvant to improve the efficacy of drugs and prevent adaptation to chronic use of drugs.

Example 10: Use of Low Dose or Standard Dose of Colchicine in Subjects with Gaucher Disease Use of colchicine for treatment of diseases in which glycosphingolipids are accumulated due to inborn error of metabolism, such as Gaucher disease Using colchicine in a low dose or in a standard dose in subjects with Gaucher disease who are naïve for therapy and follow up of platelet counts following 4 weeks of therapy.

Using colchicine in a low dose or in a standard dose in subjects with Gaucher disease who are receiving enzyme replacement therapy or substrate reduction therapy for therapy and follow up of platelet counts following 4 weeks of therapy.

The algorithm provides of a new treatment regimen of adding low dose of drugs that target the microtubules for prevention of adaptation and improving responsiveness to chronic therapies in subjects with genetic diseases and inborn error of metabolism.

In Vitro Study:
Take PBMC from naïve GD patients
incubate with ConA with and without colchicine
Test for IFNg
 IFNg measurement (ELISA) in 2 Gaucher patients as follows:
A: Lymphocytes only
B: Lymphocytes with Colchicine low dose: 0.0625 pg/ml
C: Lymphocytes with dexamethasone 250 ug/well

| P1 | | | P2 | | |
|---|---|---|---|---|---|
| A | 0.227 | 80.9 | A | 1.054 | 474.7 |
| B | 0.167 | 52.3 | B | 0.157 | 47.57 |
| C | 0.127 | 33.29 | C | 0.106 | 23.29 |

| Conc | Patient 1 | Patient 2 |
|---|---|---|
| A | 80.9 | 474.7 |
| B | 52.3 | 47.57 |
| C | 33.29 | 23.29 |

Figure 10:
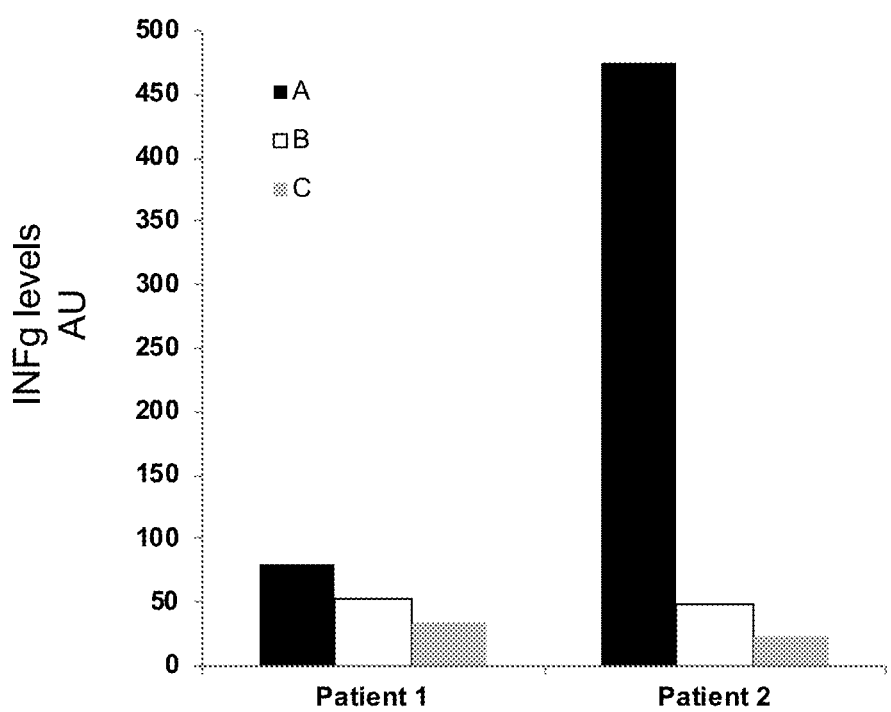
FIG. 10 shows INFg levels (arbitrary units) in patients treated with lymphocytes alone, with a combination of lymphocytes and Colchicine, or with a combination of lymphocytes and dexamethasone.

As seen from the above tables as well as from FIG. 10 low doses of colchicine and dexamethasone have a profound effect on suppressing the inflammatory effect of PBMC from patients with Gaucher disease. The effects are comparable to those of high dose steroids.

Example 11: A Controlled Phase II Trial for Alleviation of Parkinson Disease Using CBD Formulation Précis: Parkinson's disease (PD) is a degenerative disease results from the death of dopamine-generating cells in midbrain. The disease is clinically diagnosed based on its core motor symptoms: slowness of movement (bradykinesia), resting tremor, muscle rigidity and impaired gait and postural reflexes. While the diagnosis of the disease is based on its motor symptoms, certain non-motor symptoms such as sleeping disorders, constipation and impaired sense of smell could precede the motor symptoms. This period is called the pre-motor or the prodromal phase. Currently, there is no cure for Parkinson's disease. The long pre-motor phase of the disease opens a window for disease modifying therapies that would delay the appearance of the motor symptoms. Such a therapy does not exist yet.

The endocannabinoid system plays a regulatory role in a number of physiological processes and has been found altered in different pathological conditions, including movement disorders. The interactions between cannabinoids and dopamine in the basal ganglia involve modulation of other neurotransmitters, γ-aminobutyric acid, glutamate, opioids, peptides, and the activation of different receptors subtypes (cannabinoid receptor type 1 and 2). Interactions between cannabinoids and other receptor systems (transient receptor potential vanilloid type 1 cation channel, adenosine receptors, 5-hydroxytryptamine receptors) were also shown.

This study will evaluate the possibility to improve response to CBD-based formulation in patients with PD using a dosing application which works by a physician pre-determined approved therapeutic window treatment regimen.

Patients will be followed for 4 weeks and will be compared with their pre-treatment condition. During the first 2 weeks the patient will receive a constant dose of CBD formulation, during the last two weeks the patient will receive the same total daily dose using an app that will instruct him when to take the drug.

Objectives: Primary:
The primary objective of this study is to evaluate the safety and efficacy of CBD in patients with PD, and assessing the efficacy of using an app that instruct the patient on taking the drug.

Secondary:
To assess the efficacy of the regimen on efficacy parameters.

Population: 10 adult subjects (≥18 years) with Parkinson disease.
Phase: 2
Number of Sites: 1
Test Article: A therapeutic window will be determined by the physician to include a treatment regimen which is within the pre-determined approved therapeutic window.

Description of Intervention: Open-label, one-center study, 10 adults (>18) male and female with, Parkinson disease, on stable doses of other therapies and symptoms, will participate in a 4-week observation period during which no change in the drugs is permitted. The patient will begin 2-weeks treatment by taking his a CBD formulation followed by 2 weeks of taking the medications according to a app-determined schedule that is pre-set for him by his physician using the same CBD formulation changing the dose and times of taking them each day, while keeping the drugs within their therapeutic window.

Inclusion Criteria: 1. Signed informed consent.
2. Age 40-75 years.
3. At least one of the following PD prodromal signs/symptoms:
Impaired sense of smell demonstrated in objective smell test.
UPDRS III excluding action tremor >3.
Abnormal substantia nigra (SN) ultra-sound hyperechogenicity (>0.2).
Constipation based on validated scale
Thinning of the retina measured by OCT
REM sleep disorder (validated)

Exclusion Criteria: 1. Established diagnosis of Lewy body dementia (DLBD) or other neurodegenerative disease at the time of screening.
2. Significant cognitive impairments (MoCA<26 for participants with 12 years or more of education or MoCA<25 for participants with less than 12 years of education) at the time of screening.
3. History of psychosis.
4. History of exposure to lithium or anti-epileptic drugs on the previous year.
5. Clinical depression.
6. Pregnancy or lactation, or female subject at childbearing age who is unwilling to use contraceptive measures.
7. Use of another experimental treatment.
8. Unable to comply with study visits/requirements Study Endpoints: Primary Outcome Measures:
Safety measures
Improvement in clinical symptoms
Secondary Outcome Measures:
Improvement is any of the following symptoms Subject Participation Duration: A screening visit will be conducted up to 7 days before the start of the trial followed by a 2 week period of stable dose and 2 weeks treatment with an app-determined regimen with the same dose.

Estimated Time to Complete Enrollment: Estimated time from enrollment into study of the first subject to enrollment into study of the last subject: 12 months Example 11: A Controlled Phase IV Trial for Prevention of Loss of the Effect to Epilepsy Drugs Using Random Change within a Pre-Determined Approved Therapeutic Window Treatment Regimen Précis: Epilepsy is one of the most common chronic neurological diseases. One in 3 epilepsy patients have refractory seizures meaning that all anti-seizure drugs fail to control their seizures. Drug resistance in epilepsy may be related to habituation and adaptation of the target organs.

This open-labeled study will evaluate the possibility to overcome this resistance in patients with drug-resistance epilepsy by using a pre-determined treatment regimen prepared for the patient.

In the present study we will add the use of a treatment schedule prepared by the physician for each of the patients. This schedule includes a treatment regimen based on the drugs the patient is taking with a pre-determined random change in times of taking the medication keeping them within their approved therapeutic window.

Patients will be followed for three months and will be compared with their pre-treatment condition. Seizure frequency/severity will be tracked.

Objectives: Primary:
The primary objective of this study is to evaluate the safety and efficacy of using a pre-determined treatment regimen when administered as adjunctive therapy in patients that have exhausted the majority of approved anti-epileptic drug treatment options.

Secondary:
To assess the efficacy of the regimen on seizure frequency/severity.

Population: 20 adult subjects (≥18 years) with drug-resistant epilepsy.
Phase: 4
Number of Sites: 2
Test Article: A therapy schedule prepared by the physician for each of the patients, that includes a treatment regimen based on the drugs the patient is taking with a random change in times of taking the medications and their dose, which are within their pre-determined approved therapeutic window.

Description of Intervention: Open-label, two-center study, 20 adults (>18) male and female with, intractable epilepsy, on stable doses of antiepileptic drugs (AEDs), will participate in a 4-week observation period during which no change in the drugs is permitted. The patient will then begin 10-week treatment by taking his medications according to a random schedule that is pre-set for him by his physician using the same drugs the patient is taking and only changing the dose and times of taking them each day, while keeping the drugs within their therapeutic window.

Figure 11:
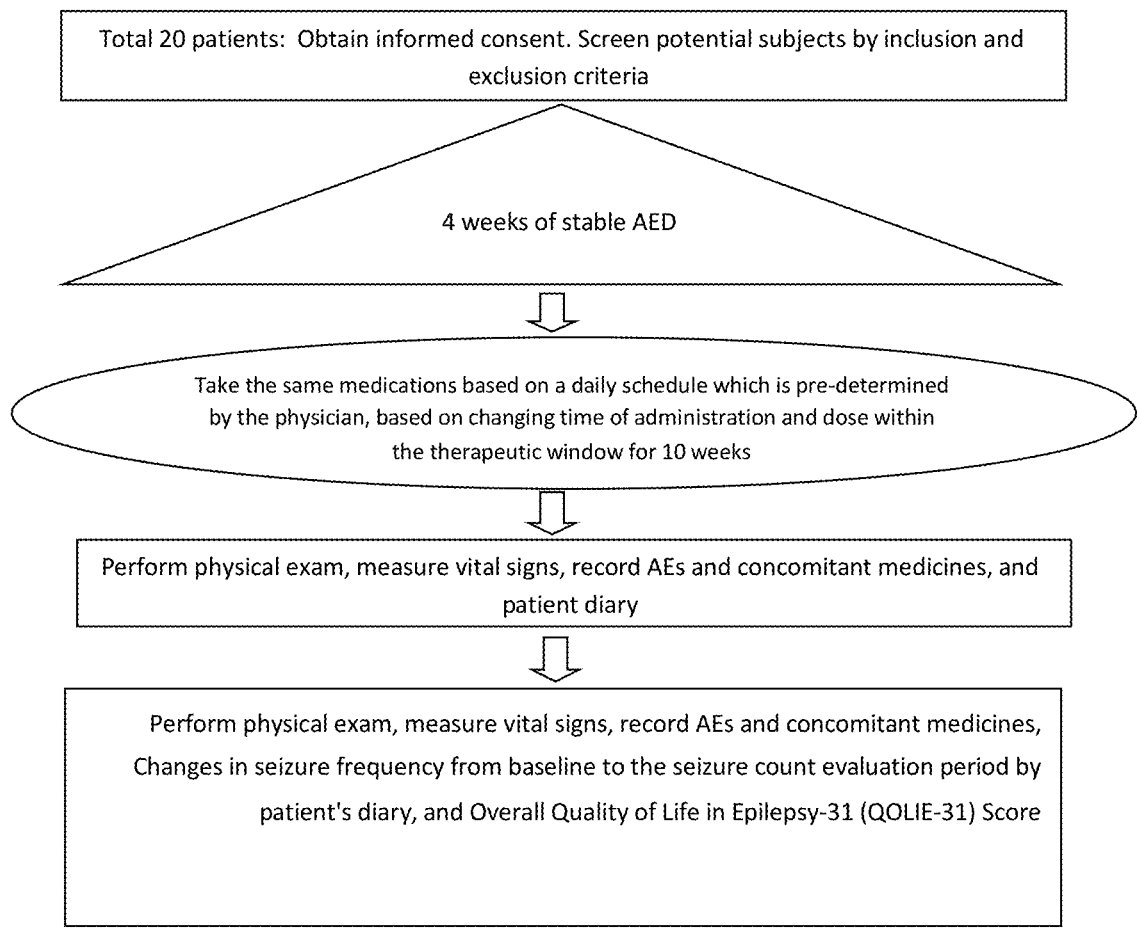
FIG. 11 schematically illustrates the study design of a trial for preventing loss of epilepsy drug treatment efficacy according to some embodiments.

During the study the patient will fill a seizure diary daily. A schematic illustration of the study design is shown in FIG. 11.

| Inclusion Criteria: | Ages Eligible for Study: | 18 Years to 80 Years (Adult) |
| --- | --- | --- |
| | Sexes Eligible for Study: | All |

1. Patients in whom seizures are not controlled by their anti-seizure medication
2. Must have at least 2 seizures per month
3. History of any of the following seizure types: tonic, clonic, tonic-clonic in the form of partial seizures, partial seizures secondarily generalized or primary generalized, complex partial seizures and drop attacks (tonic/atonic)
4. At least four clinically countable seizures within 4 weeks of study entry (tonic, clonic, tonic-clonic in the form of partial seizures, partial seizures secondarily generalized or primary generalized and/or complex partial seizures and drop attacks (tonic/atonic))
5. Subject on a stable regimen of 1-4 concomitant antiepileptic drugs (AEDs) for a minimum of 4 weeks prior to enrollment
6. History of treatment with at least two AEDs, including one trial of a combination of at least two concomitant drugs, without successful seizure control
7. Subjects with vagal nerve stimulation system must be on stable settings for a minimum of 6 months prior to enrollment
8. RNS deep brain stimulation, or the ketogenic diet can be considered equivalent to a drug trial and must be on a stable ratio for a minimum of 3 months prior to enrollment
9. Completed seizure diary for four weeks (±3 days) prior to initiation of the dose titration period (visit 2). Subject will be considered a screen failure if seizure diary was not appropriately completed
10. Anti-epileptic drugs at stable doses for a minimum of 4 weeks prior to enrollment.

Exclusion Criteria: 1. Neurodegenerative or deteriorated neurological disease
2. Psychosis or past psychotic event and/or anxiety disorder
3. Current or history of drug abuse/addiction
4. Abnormal creatinine
5. Any chronic ophthalmology disease
6. The subject is currently using or has used *cannabis*-based or synthetic cannabinoid within three months of study entry
7. Renal, hepatic [ALT/AST>2× upper limit of normal (ULN), bilirubin >2×ULN], pancreatic dysfunctions or laboratory test abnormalities, at the investigator's discretion
8. Subject is pregnant, lactating, or planning a pregnancy during the course of the study or within 3 months of study completion
9. Subject is currently enrolled in, or has not yet completed a period of at least 60 days since ending another investigational device or drug trial(s)
10. Unable to comply with study visits/requirements
11. Diagnosis of Dravet Syndrome, Lennox-Gastaut syndrome, or any other congenital or childhood syndrome will be excluded completely from this trial
12. Female subjects who are pregnant will be excluded from the study. If a female subject is able to become pregnant, she will be given a serum pregnancy test before entry into the study. Female subjects will be informed not to become pregnant while on the trial. Female subjects must tell the investigator and consult an obstetrician or maternal-fetal specialist if they become pregnant during the study.

Study Endpoints: Primary Outcome Measures:
Change in seizure frequency from baseline to the seizure count evaluation period Secondary Outcome Measures:
1. Change in seizure frequency from baseline to the seizure count evaluation period
2. Overall Quality of Life in Epilepsy-31 (QOLIE-31) Score in Patients with Baseline & at Least One Post-baseline QOLIE Assessment
QOLIE-31 contains 7 multi-item scales that tap the following health concepts: overall quality of life, emotional well-being, social functioning, energy/fatigue, worry about seizure, cognitive functioning, medication effects. Range of values 0-100. Higher scores reflect better quality of life; lower ones, worse quality of life.
3. Changes in the number of Anti-epileptic Drugs prescribed
4. Changes in Anti-Epileptic Drugs (AEDs) in patients with less than a 50% reduction in seizures.

Subject Participation Duration: A screening visit will be conducted up to 7 days before the start of the trial followed by a 4 week period in which AEDs cannot be changed and followed by 10 weeks of intervention.

Estimated Time to Complete Enrollment: Estimated time from enrollment into study of the first subject to enrollment into study of the last subject: 12 months Statistical Analysis Definition of Analysis Population:
The safety and efficacy population will include all randomized subjects who participated at least one week in the trial.

General Statistical Methods:
All measured variables and derived parameters will be listed individually and, if appropriate, tabulated by descriptive statistics.

Primary Endpoint Analysis
Analysis for the primary endpoint will be descriptive in nature and summarized in appropriate tables.

Secondary Endpoint Analysis
The paired T-test will be applied for testing the statistical significance of the changes from baseline (Day 1) to each of the later visits for all numeric secondary endpoints within each treatment group.

The ANOVA test will be applied for testing the statistical significance between the treatment groups in all secondary endpoints.

All tests applied will be two-tailed, and p-value of 5% or less will be considered statistically significant.

|  | Screening | Basline period (4 weeks) Visit | Intervention | | |
|---|---|---|---|---|---|
|  | 1 | 2 | 3 | 4 | 5 |
|  |  | Study week | | | |
|  | −5 | 0 | 4 | 8 | 10 |
| Informed consent | X |  |  |  |  |
| Inclusion/exclusion criteria | X |  |  |  |  |
| Demographic & medical history | X |  |  |  |  |
| Randomization |  | X |  |  |  |
| Study Intervention |  |  | X | X | X |
| Physical examination | X | X | X | X | X |
| Vital signs | X | X | X | X | X |
| Adverse events |  |  | X | X | X |
| Concomitant medications | X | X | X | X | X |
| Urine β-hCG | X |  |  |  |  |
| Subject Diary |  | X | X | X | X |
| Epilepsy-31 (QOLIE-31) Score |  | X |  |  | X |

Example 12: Effect of Treatment with Low Dose Colchicine on a Model of Type 2 Diabetes and High Fat Diet Protocol:
  Give colchicine at the end of the experiment for two weeks to 4 mice who were on a High fat diet and developed diabetes and fatty liver disease.
  Mice are treated with a dose that had no anti-inflammatory effect.
  Test for glucose, ALT and cholesterol levels at the end of the two weeks.

|  | ALT (IU) | Cholesterol (mg %) | Glucose (mg %) |
|---|---|---|---|
| Control | 278 | 342 | 190 |
| Colchicine | 103 | 100 | 155 |

Figure 12:
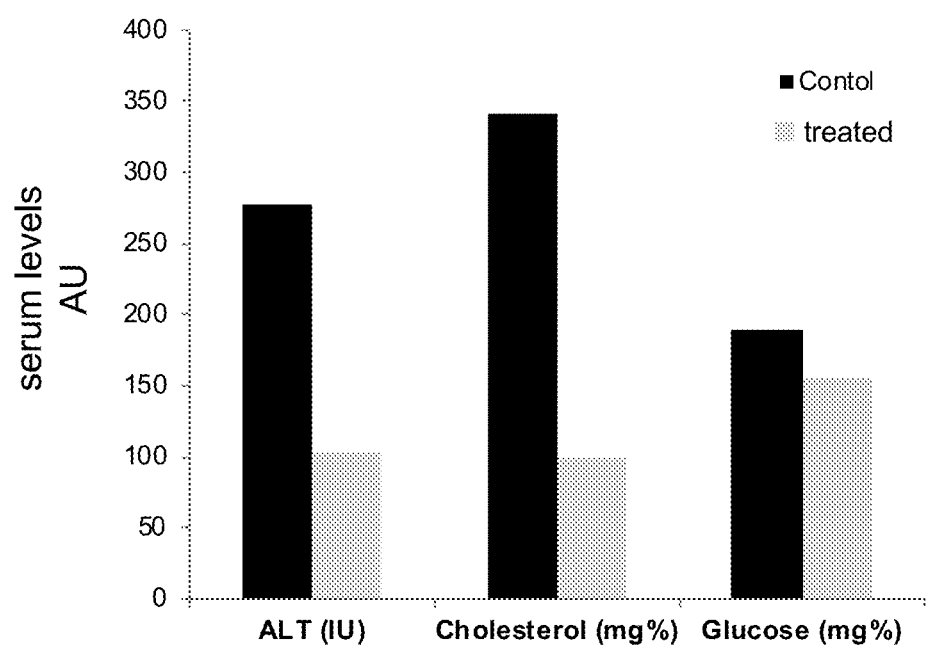
FIG. 12 shows ALT levels, cholesterol levels and glucose levels (arbitrary units) in mice left untreated or treated with a low dose Colchicine.

The table above as well as FIG. 12 demonstrate that a new treatment regimen using a sub therapeutic amount of drugs that target the microtubules, in a dose that has no effect on the microtubules or has any anti-inflammatory effect an effect on chronic disease, diabetes, and fatty liver, can be achieved.

We claim:

1. A computer implemented method of administering one or more drugs comprising Colchicine to a subject for a medical condition in a manner that prevents, mitigates or treats partial or complete loss of effect of the one or more drugs due to adaptation, tolerance, and/or tachyphylaxis, the method comprising:
  receiving a plurality of physiological or pathological parameters of the subject;
  applying a deep learning algorithm on the plurality of physiological or pathological parameters,
  wherein the deep learning algorithm is configured to output an irregular subject-specific administration regimen of one or more drugs,
  wherein the irregular administration regimen comprises drug administration parameters, which are configured to randomly alter a dose and one or both of a time of and a mode of administration of the one or more drugs in a subject-specific random way, thereby prevent, mitigate or treat partial or complete loss of effect of the one or more drugs administered to or used by a subject in need thereof due to adaptation, tolerance, and/or tachyphylaxis,
  administering the one or more drugs to the subject in accordance with the irregular subject-specific administration regimen, thereby preventing, mitigating or treating partial or complete loss of effect in the subject in need thereof,
  wherein the altering of the dose of Colchicine at times is to a dose lower than and outside of the therapeutic range of Colchicine for the medical condition.

2. The method of claim 1, further comprising updating the administration regimen based on newly received values of the plurality of physiological or pathological parameters.

3. The method of claim 1, wherein the wherein the drug administration parameters are configured to randomly alter the dose, the time of administration and the mode of administration of the one or more drugs.

4. The method of claim 1, wherein the deep learning algorithm further considers personal data selected from the group consisting of: age, weight, periodic caloric intake and output, gender, ethnicity, geography, pathological history and/or state, temperature, metabolic rate, glucose levels, blood tests and any physiological or any pathological or physiological biomarkers or parameters that can be measured, that are directly or indirectly associated with the physiological target or with the chronic disease.

5. The method of claim 1, wherein at least one of the physiological or pathological parameters is obtained from a sensor.

6. The method of claim 1, wherein the Colchicine is a sole therapy for the medical condition.

7. The method of claim 1, for treatment of obesity, infections, metabolic, endocrinology, malignant, immune-mediated, inflammatory condition, inborn error of metabolism, pain, microbiome-related disorders, neurological disease, fibrosis in any organ, any type of disease in which circadian rhythm is relevant or any combination thereof.

8. The method of claim 1, wherein the one or more drugs are drugs that target microtubules.

9. The method of claim 1, wherein the one or more drugs are drugs that target glycosphingolipids.

10. The method of claim 1, wherein Colchicine is an adjuvant.

11. A system for preventing, mitigating or treating partial or complete loss of effect of one or more drugs comprising Colchicine administered to or used by a subject in need thereof for a medical condition due to adaptation, tolerance, and/or tachyphylaxis, the system comprising a processing circuit configured to:
  receive a plurality of physiological or pathological parameters of the subject;
  apply a deep learning algorithm on the plurality of physiological or pathological parameters,
  wherein the deep learning algorithm is configured to output an irregular subject-specific administration regimen of the one or more drugs,
  wherein the irregular administration regimen comprises drug administration parameters, which are configured to randomly alter a dose and one or both of a time of and a mode of administration of the one or more drugs in a subject-specific random way, thereby prevent, mitigate or treat partial or complete loss of effect of the one or more drugs administered to or used by a subject in need thereof due to adaptation, tolerance, and/or tachyphylaxis, wherein the system outputs the irregular subject-specific administration regimen and wherein the one or more drugs comprising Colchicine is administered to the subject in the need thereof in accordance with the irregular subject-specific administration regimen, thereby preventing, mitigating or treating partial or complete loss of effect in the subject in need thereof, wherein the altering of the dose of Colchicine at times is to a dose lower than and outside of the therapeutic range of Colchicine for the medical condition.

12. The system of claim 11, wherein the medical condition is obesity, infections, metabolic, endocrinology, malignant, immune-mediated, inflammatory condition, inborn error of metabolism, pain, microbiome-related disorders, neurological disease, fibrosis in any organ, any type of disease in which circadian rhythm is relevant or any combination thereof.

13. The system of claim 12, wherein Colchicine is a drug that targets microtubules.

14. The system of claim 12, wherein Colchicine is a drug that targets glycosphingolipids.

15. The system of claim 12, wherein the drug administration parameters are configured to randomly alter the dose, the time of administration and the mode of administration of the one or more drugs.

16. The system of claim 11, further comprising an alert module configured to provide instructions to a user regarding a change in the administration regimen of the one or more drugs.

17. The system of claim 16, further comprising a communication unit configured to deliver the alert, wherein the alert is operable via a cloud based alert system connected to a medical device or to a drug box configured to provide instructions to a user regarding the administration regimen of the one or more drugs.

* * * * *